(12) United States Patent
Larsen et al.

(10) Patent No.: US 7,462,596 B2
(45) Date of Patent: Dec. 9, 2008

(54) PHARMACEUTICAL COMPOSITIONS COMPRISING MANNOSE BINDING LECTIN

(75) Inventors: Jesper Lund Larsen, København Ø (DK); Leif Kongerslev, Birkerød (DK)

(73) Assignee: Natimmune A/S, Copenhagen (DK)

( * ) Notice: Subject to any disclaimer, the term of this patent is extended or adjusted under 35 U.S.C. 154(b) by 54 days.

(21) Appl. No.: 10/388,322

(22) Filed: Mar. 14, 2003

(65) Prior Publication Data
US 2004/0006009 A1    Jan. 8, 2004

(30) Foreign Application Priority Data
Mar. 15, 2002    (DK) ............................... 2002 00414

(51) Int. Cl.
*A61K 38/16*    (2006.01)
(52) U.S. Cl. ........................................................... 514/8
(58) Field of Classification Search ...................... 514/8
See application file for complete search history.

(56) References Cited

U.S. PATENT DOCUMENTS

| | | | | |
|---|---|---|---|---|
| 6,297,024 B1 * | 10/2001 | Hugli et al. | ................... | 435/23 |
| 6,429,192 B1 * | 8/2002 | Laursen | .......................... | 514/8 |
| 6,562,784 B1 * | 5/2003 | Thiel et al. | ..................... | 514/8 |
| 2003/0198998 A1 * | 10/2003 | Uttenthal | .................... | 435/7.1 |

FOREIGN PATENT DOCUMENTS

WO        WO 99/64453    * 12/1999

OTHER PUBLICATIONS

Rudinger, J. "Characteristics of the amino acids as components of a peptide hormone sequence" in Peptide Hormones, J. A. Parsons, Editor. Biological Council The Co-ordinating Committee for Symposia on Drug Action. Jun. 1976, pp. A0 and 1-7.*
Weis et al. Physical Characterization and Crystallization of the Carbohydrate-recognition Domain of a Mannose-binding Protein from Rat. J Biol Chem 1991, vol. 266, No. 31, pp. 20678-20686.*
Vorup-Jensen et al. Distinct Pathways of Mannan-Binding Lectin (MBL)- and C1-Complex Autoactivation Revealed by Reconstitution of MBL with Recombinant MBL-Associated Serine Protease-2. J Immunol 2000. vol. 165, pp. 2093-2100.*
Tan et al. Improvements on the purification of mannan-binding lectin and demostration of its Ca2+-independent association with a C1s-like serine protease. Biochem J. 1996. vol. 319, pp. 329-332.*
Kilpatrick. Mannan-binding lectin and its role in innate immunity. Transfusion Medicine. 2002. vol. 12, pp. 335-351.*
SIGMA. Designing Custom Peptides. http://www.sigma-genosys.com/peptide_design.asp (Accessed Dec. 16, 2004) 2 pages.*
HJC Berendsen. A Glimpse of the Holy Grail? Science (1998) vol. 282., pp. 642-643.*
D Voet and JG Voet. Biochemistry, 2nd edition, (1995) pp. 235-241.*
DE Smilek et al. A single amino acid change in a myelin basic peptide confers the capacity to prevent rather than induce experimental autoimmune encephalomyelitis. Proc. Natl. Acad. Sci. USA (1991) vol. 88, pp. 9633-9637.*
Dictionary.com. Entries for "stable" http://dictionary.reference.com/search?q=stable (Accessed Jul. 20, 2005) 1 page.*
Akers et al. Sterile Formulation (Chapter 14) in Vogel et al, Fermentation and Biochemical Engineering Handbook—Principles, Process Design, and Equipment (2nd Edition). 1997, pp. 616-634 and 2 cover pages.*
Laursen, I. MBL production from human plasma. Mar. 20, 2003. Royal College of Physicians of Edinburgh. Therapeutic Applications oof Mannan-Binding Lectin. S4 and pp. 1-2.*
Laursen, Inga, "Mannen-binding lectin, a new plasma product: production process and clinical application", *Plasma Product Biotechnology (PPB) Meeting*, May 14-17, 2001, pp. 15-17.
Laursen, I, "Mannan-binding lectin (MBL) production from human plasma", *Biochemical Society Transactions*, vol. 31, part 4, pp. 758-762, 2003.

* cited by examiner

*Primary Examiner*—Andrew D Kosar
*Assistant Examiner*—Marcela M Cordero Garcia
(74) *Attorney, Agent, or Firm*—Iver P. Cooper

(57) ABSTRACT

The present invention relates to pharmaceutical compositions comprising MBL and/or MBL variants. In particular the invention relates to pharmaceutical compositions comprising at least 200 μg/ml protein containing material, wherein mannan binding lectin (MBL) and/or MBL variants constitutes at least 35% (w/w) of the total protein; or to compositions comprising at least 400 μg/ml mannan binding lectin (MBL) and/or MBL variants. In addition the invention relates to pharmaceutical compositions comprising MBL and/or MBL variants and divalent cations. The invention also describes methods of preparing said compositions.

The pharmaceutical compositions according to the invention may for example be used in methods of treatment of a number of different clinical conditions including infections. Uses of the compositions for preparation of medicaments for treatment of a clinical condition are also described.

106 Claims, 3 Drawing Sheets

PHARMACEUTICAL COMPOSITIONS COMPRISING MANNOSE BINDING LECTIN

FIELD OF INVENTION

The present invention relates to pharmaceutical compositions comprising mannose binding lectin. Furthermore, the invention relates to methods of treatment of a clinical condition using said pharmaceutical compositions and to use of the pharmaceutical compositions for the preparation of a medicament.

BACKGROUND OF INVENTION

MBL is a protein of the collectin family and characterised by an oligomeric structure of subunits. Each subunit consists of 3 identical polypeptides each consisting of a calcium-dependent, C-type carbohydrate-recognition domain (CRD), attached to a collagenous rod.

The number of subunits in an MBL molecule is varying (Lipscombe R J, et al, 1995), but it has been suggested that the biologically active polypeptide is an oligomer consisting of more than three subunits. Naturally occurring MBL in plasma comprises mainly oligomers of more than three subunits, and in addition denatured and structurally impaired protein forms leading to bands on for example SDS gels between the dominating MBL bands corresponding to the higher oligomers.

Recombinantly produced MBL reveals an oligomer variation similar to plasma-derived MBL (Vorup-Jensen T et al., 2001). However, usually recombinantly produced MBL has a higher content of low-mass forms than do plasma derived MBL. Low-mass forms of MBL include for example single polypeptide chains, single subunits, and dimeric subunits.

MBL is structurally related to the C1q subcomponent of component C1 of complement, and it appears that MBL activates the complement system via associated serine protease termed MASPs (Matsushita, M., 1992) or p100 (Ji, Y -H. et al., 1993), which are similar to the C1r and C1s components of the classical pathway. The MBL complement activation pathway is called the MBLectin pathway. According to the mechanism postulated for this pathway, MBL binds to specific carbohydrate structures found on the surface of a range of microorganisms including bacteria, yeast, parasitic protozoa and viruses (Turner, M. W, 1996), and its antimicrobial activity results from activation of the terminal, lytic complement pathway components (Kawasaki, N et al., 1989) or promoting phagocytosis (Kuhiman, M et al., 1989).

Reportedly, the level of MBL in plasma may be genetically determined (Sumiya, M et al., 1991, Lipscombe, R. J. et al., 1992, Madsen H. O. et al. 1994). MBL deficiency is associated with susceptibility to frequent infections with a variety of microorganisms in childhood (Super, M et al., 1989, Garred, P. et al., 1995), and possibly, in adults (Garred, P. et al., 1995, Summerfield, J. A. et al. 1995). Recent information associates MBL deficiency with HIV infection and with more rapid death following development of AIDS (Nielsen, S. L et al., 1995, Garred, P et al., 1997). MBL binds to the a galactosyl form of IgG (G0), which is found at elevated concentrations in rheumatoid arthritis patients, and then activates complement (Malhotra, R et al., 1995). MBL deficiency is also associated with a predisposition to recurrent spontaneous abortions (Kilpatrick, D. C et al., 1995), and also to development of systemic lupus erythrematosus (Davies, E. J et al., 1995).

MASP-1 (MBL-associated serine protease 1) is a serine protease similar in structure to C1r and C1s of the complement pathway although it has a histidine loop structure of the type found in trypsin and trypsin-like serine proteases. MASP-1 has been found to be involved in complement activation by MBL. A cDNA clone encoding MASP-1 has been reported that encodes a putative leader peptide of 19 amino acids followed by 680 amino acid residues predicted to form the mature peptide.

MASP-2 (MBL-associated serine protease 2) (Thiel, S et al., 1997) is a serine protease similar in structure to C1r and C1s of the complement pathway. Like these, and contrary to MASP-1, it has no histidine loop structure of the type found in trypsin and trypsin-like serine proteases. MASP-2 has been found to be involved in complement activation by MBL. MASP-3 shows some homology with MASP-1 and MASP-2 and the two C1q-associated serine proteases, C1r and C1s.

MBL purified from serum has previously been used in a pharmaceutical formulation furthermore containing human serum albumin to treat two MBL deficient individuals and said MBL treatment resulted in significant reduction of infections (Valdimarson et al., 1998). In addition, various other pharmaceutical MBL formulations have been described in the prior art:

Valdimarsson et al. describes infusion of a solution containing 200 µg/ml MBL in 0.15 M NaCl and 1% w/v (=10 mg/ml) human serum albumin.

U.S. Pat. No. 5,270,199 describes an MBL formulation comprising 5 to 100 µg/ml MBL and/or MBL fragment.

WO 99/64453 describes various MBL formulations comprising MBL and a stabilising agent. As preferred example is mentioned a formulation comprising 300 to 400 µg/ml MBL in PBS with 0.5% w/v albumin (=5 mg/ml).

However, these MBL formulations comprise either low amounts of MBL and/or high concentration of other proteins.

SUMMARY OF INVENTION

However, there is a need for MBL formulations, comprising stable MBL, in particular such formulations comprising reduced amounts of protein containing stabilisers, such as for example reduced amounts of human serum albumin.

Almost all pharmaceutical formulations comprising proteins or polypeptides as the active ingredient do also comprise one or more stabilisers of said protein or polypeptide. In particular, said stabilisers may be detergents or protein containing stabilisers. For many purposes however, it is desirable to omit or reduce the amount of different additives, such as stabilisers for use in pharmaceutical compositions, in particular the amount of protein containing stabilisers, however frequently reduction of protein containing stabilisers results in reduced stability of the active protein component.

The inventors have developed methods for producing highly concentrated MBL and surprisingly, the inventors have shown that MBL formulations comprising high MBL concentrations may be sufficiently stable to be used in pharmaceutical formulations even if no or only a reduced amount of protein containing stabiliser is added.

Accordingly, it is a first objective of the present invention to provide pharmaceutical compositions comprising pharmaceutically acceptable additives and a) at least 200 µg/ml protein containing material, wherein mannan binding lectin (MBL) and/or MBL variants constitutes at least 35% (w/w) of the total protein; or b) at least 400 µg/ml mannan binding lectin (MBL) and/or MBL variants It is a second objective of the present invention to provide pharmaceutical compositions comprising pharmaceutically acceptable additives; and mannan binding lectin (MBL) and/or MBL variants; and at least one divalent cation.

It is a third objective of the present invention to provide a process for preparation of said pharmaceutical compositions, comprising the steps of
   a) Providing mannan binding lectin (MBL) and/or MBL variants
   b) Mixing said MBL and/or MBL variants with pharmaceutical acceptable additives and optionally with divalent cations
   c) And thereby obtaining said pharmaceutical compositions It is a further objective of the present invention to provide methods of treatment of a clinical condition in an individual in need thereof, comprising administration of said pharmaceutical compositions. The treatment may be selected from the group consisting of curative, ameliorating, relieving and preventive treatment and supplement treatment.

It is a still further objective of the present invention to provide use of the above mentioned composition, for the preparation of a medicament for the treatment of a clinical condition in an individual in need thereof.

It is a furthermore an objective of the present invention to provide a medicament for the treatment of a clinical condition in an individual in need thereof comprising a composition as described above.

It is furthermore an objective of the present invention to provide methods of diagnosis involving administration of the pharmaceutical compositions mentioned herein above or to provide uses of said pharmaceutical compositions for diagnostic purposes.

SHORT DESCRIPTION OF FIGURES

Figure 3A:
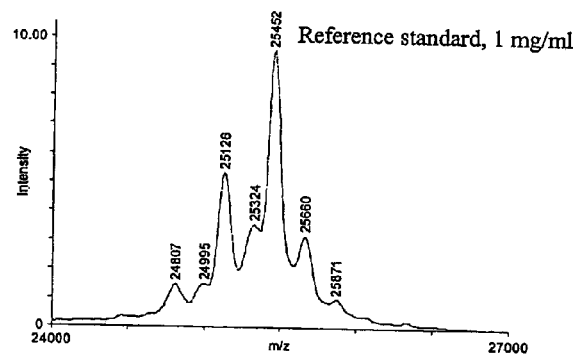
Figure 3B:
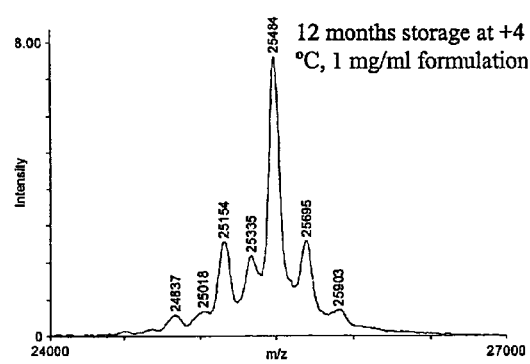
Figure 3C:
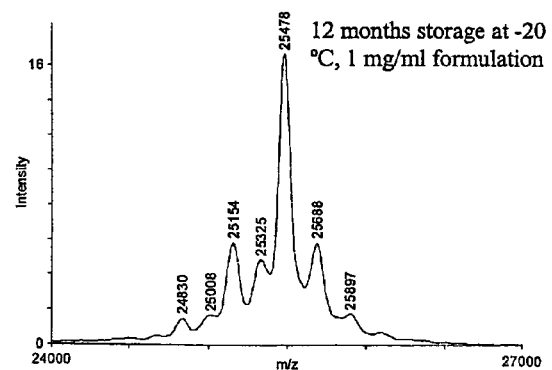

FIGS. 3A-3C illustrate mass spectrometry data. Similar peaks for the reference FIG. 3A and the 12 months MBL samples indicate no changes in MBL polypeptide chain during storage at 4° C. (FIG. 3B) and at −20° C. (FIG. 3C). Short description of sequence listing
   SEQ ID NO: 1: Human MBL protein sequence
   SEQ ID NO: 2: Human MASP-1 protein sequence
   SEQ ID NO: 3: Human MASP-2 protein sequence
   SEQ ID NO: 4: Human MASP-3 protein sequence

DETAILED DESCRIPTION OF THE INVENTION

MBL and MBL Variants

The present invention i.a. provides pharmaceutical compositions comprising MBL and/or MBL variants. The pharmaceutical compositions should in general comprise a high MBL concentration, for example the composition may comprises at least 200 µg/ml, such as at least 250 µg/ml, for example at least 300 µg/ml, such as at least 500 µg/ml, for example at least 750 µg/ml, such as at least 1000 µg/ml, for example at least 1300 µg/ml MBL and/or MBL variants.

Accordingly, the composition may comprise in the range from 200 to 10,000 µg/ml, such as from 200 to 5000 µg/ml, for example from 200 to 3000 µg/ml, such as from 200 to 2000 µg/ml, for example from 200 to 1500 µg/ml MBL and/or MBL variants.

In embodiments of the present invention wherein the pharmaceutical compositions comprises a divalent cation it is preferred that said compositions comprises at least 10 µg/ml, such as at least 25 µg/ml, for example at least 50 µg/ml, such as at least 100 µg/ml, for example at least 150 µg/ml, such as at least 200 µg/ml, such as at least 250 µg/ml, for example at least 300 µg/ml, such as at least 500 µg/ml, for example at least 750 µg/ml, such as at least 1000 µg/ml, such as at least 1500 µg/ml, for example at least 2000 µg/ml, such as at least 2500 µg/ml, for example at least 3000 µg/ml, such as at least 3500 µg/ml, for example at least 4000 µg/ml, such as at least 5000 µg/ml, for example at least 6000 µg/ml, such as at least 7000 µg/ml, for example at least 8000 µg/ml, such as at least 9000 µg/ml, for example at least 10000 µg/ml MBL and/or MBL variants.

The concentration of MBL should in general be determined by determining and/or calculating the weight of the amino acids constituting MBL. In general, the weight is calculated to correspond to the non-glycosylated form of MBL. Hence in general the weight of MBL does not include any glycosylation, and it does not include water content. In one embodiment the concentration of MBL may be determined using an amino acid analysis as described herein below.

Estimation of MBL Concentration by Amino Acid Analysis:
Not all amino acids might be estimated in an amino acid analysis—however, usually the mass of the non-detectable amino acids might easily be estimated from the composition of the detected amino acids when the concentration of a pure or rather pure MBL solution is determined.

The estimation of MBL concentration may be performed according to a number of different methods. Preferably, one of the two methods described herein below may be employed, more preferably method 2 described herein below may be employed.

The amount of carbohydrate is usually not estimated, i.e. the stated protein concentration will usually only represent the peptide content alone. However, it is possible to determine the total mass of peptide+carbohydrate from the amount of amino acids.

Non-Detectable Amino Acids:
   When estimating MBL, non-detectable amino acids are
   Tryptophane (Trp is hydrolyzed in acid); 3 Trp are present in the polypeptide chain
   Histidine (His is co-eluting with Tris); only one His is present in the polypeptide chain
   Hydroxylysine (Hyl is not applied during calibration); max 4 Hyl might be present in the polypeptide chain
   Hydroxyproline (Hyp); max 8, typically 4, Hyp are present in the polypeptide chain
   Detectable—but uncertainly estimated—amino acids are
   Lysine (Lys are partly hydroxylized); 15-19 Lys are present in the polypeptide chain; max 4 Lys might be hydroxylated
   Proline (Pro are partly hydroxylized); 10-18 Pro are present in the polypeptide chain; max 8 Pro might be hydroxylated.

Method 1:
   Moles of detectable amino acids and moles of non-detectable amino acids in the analyzed sample:

Non-detectable amino acids=Trp, His, Hyp and Hyl: It is assumed that 4 Hyp, 4 Hyl, 14 Pro, and 15 Lys are present in average.

NonDetectedMoles=[Trp]+[His]+[Hyp]+[Hyl]=3+1+4+4=12

CorrectionFactor for NonDetectedMoles=AllMoles/
  DetectedMoles=AllMoles/(AllMoles-NonDe-
  tectedMoles)=228/(228−12)=1.0556 Non-detect-
  able amino acids=Trp, His, Hyp and Hyl:

NonDetectedMass=[MTrp]+[MHis]+[MHyp]+[MHyl]
  =3*186.21+1*137.14+4*113.11+4*144.17=1725.

$$\begin{aligned}DetectedMass &= [MAsx] + [MThr] + [MSer] + [MGlx] + [MPro] + \\ &\quad [MGly] + [MAla] + [MCys] + [MVal] + [MMet] + \\ &\quad [MIle] + [MLeu] + [MTyr] + [MPhe] + [MLys] + \\ &\quad [MArg] \\ &= 25*115.09 + 15*101.11 + 13*87.08 + \\ &\quad 27*129.12 + 14*97.12 + 31*57.05 + 16*71.08 + \\ &\quad 7*103.15 + 10*99.13 + 2*131.20 + 8*113.16 + \\ &\quad 17*113.16 + 1*163.18 + 9*147.18 + 15*128.17 + \\ &\quad 6*156.19 \\ &= 22429.93\end{aligned}$$

CorrectionFactor for NonDetectedMass=AllMass/
  DetectedMass=(Detected−Mass+NonDetected-
  Mass)/DetectedMass=1.0769

Method 2:

Non-detectable amino acids=Trp, His, Pro/Hyp and
  Lys/Hyl: It is assumed that 4 Hyp, 4 Hyl, 14 Pro,
  and 15 Lys are present in average.

NonDetectedMoles=[Trp]+[His]+[Pro/Hyp]+[Lys/
  Hyl]=3+1+18+19=41

CorrectionFactor for NonDetectedMoles=AllMoles/
  DetectedMoles=All−Moles/(AllMoles-NonDe-
  tectedMoles)=228/(228−41)=1.2193

Mass of detectable amino acids and mass of non-detectable amino acids in the analyzed sample:

For each amino acid, mass is estimated as moles times
  molar mass (corrected for the missing peptid
  bond water). For example: [MThr]=[Thr]*
  (119.12−18.01)=[Thr]*101.11

Non-detectable amino acids=Trp, His, Pro/Hyp and
  Lys/Hyl:

NonDetectedMass=[MTrp]+[MHis]+[MPro]+
  [MHyp]+[MLys]+[MHyl]=3*186.21+1*137.18+
  97.12+19*128.17=4879.16

$$\begin{aligned}DetectedMass &= [MAsx] + [MThr] + [MSer] + [MGlx] + [MGly] + \\ &\quad [MAla] + [MCys] + [MVal] + [MMet] + [MIle] + \\ &\quad [MLeu] + [MTyr] + [MPhe] + [MArg] \\ &= 25*115.09 + 15*101.11 + 13*87.08 + \\ &\quad 27*129.12 + 31*57.05 + 16*71.08 + 7*103.15 + \\ &\quad 10*99.13 + 2*131.20 + 8*113.16 + 17*113.16 + \\ &\quad 1*163.18 + 9*147.18 + 6*156.19 \\ &= 19147.70\end{aligned}$$

CorrectionFactor for NonDetectedMass=AllMass/
  DetectedMass=(Detected−Mass+NonDetected-
  Mass)/DetectedMass=1.2548

Comparison of Evaluation Method 1 and Method 2:

Method 1 is based on estimates of appr. 95% of the amino acids, while Method 2 is based on estimates of only appr. 75% of the amino acids.

In general, all performed amino acid content estimations are calculated by both methods, and no significant difference in results are usually observed. Method 2 makes no assumptions on content of Hyl and Hyp, and is therefore preferred.

For certain purposes the concentration of MBL is given in molar rather than as weight/volume. Because MBL may be present as oligomer comprising different amounts of subunits it is difficult to define 1 mole of MBL. Within the scope of the present invention it is preferred that 1 mole MBL refers to 1 mole of individual MBL polypeptide chains. Said individual MBL polypeptide chains may be non-glycosylated, partly glycosylated or fully glycosylated. It is preferred that molarity of MBL is calculated anticipating that MBL is not glycosylated.

The molecular weight of non-glycosylated individual MBL polypeptide chains is 24800 Da. The molecular weight of fully-glycosylated individual MBL polypeptide chains is 25900 Da. The molecular weight of the most commonly occurring form of glycosylated individual MBL polypeptide chains is 25500 Da.

Hence, dependent on the glycosylation status of MBL 1 mg/ml MBL corresponds to in the range of 38 to 41 µM, preferably in the range of 38.6 to 40.3 µM. For most practical applications 1 mg/mL MBL corresponds to around 39.2 µM. However, 1 mg/ml unglycosylated MBL corresponds to around 40.3 µM, whereas 1 mg/mL fully glycosylated MBL corresponds to around 38.6 µM.

The above calculations refer to MBL of SEQ ID No. 1.

However, it is apparent that the methods may be adapted to estimate the concentration of MBL fragments and/or variants.

For many purposes it is desirable that the pharmaceutical composition comprises a reduced amount of proteins other than MBL (see herein below).

Accordingly, pharmaceutical composition are preferred, wherein MBL or MBL variants constitutes at least 35% (w/w), such as at least 40% (w/w), for example at least 50% (w/w), such as at least 60% (w/w), for example at least 70% (w/w), such as at least 80% (w/w), for example at least 90% (w/w), such as at least 95% (w/w), for example at least 98% (w/w), such as at least 99% (w/w), for example at least 99.5% (w/w), such as at least 99.8% (w/w) of the total protein.

In one embodiment of the invention MBL constitutes essentially all of the total protein. The term "essentially all" is meant to encompass "all detectable", preferably all protein detectable by coomassie brilliant blue staining.

In another embodiment the pharmaceutical composition may comprise commonly used protein additives, for example proteins acting as stabilisers or protein containing stabilisers. Proteins useful as stabilisers includes for example human serum albumin or other kinds of serum albumin. Furthermore, protein containing stabilisers may be provided in crude human serum or fractions thereof.

It is in general important for the stability of protein containing pharmaceutical formulations, that they comprise a suitable concentration of proteins. In general, if the concentration of the protein of interest is low, there is a significant risk of unspecific adhesion of the protein of interest to surfaces of a storage container or the like. Furthermore, protein-protein interactions stabilises the 3 dimensional structure of proteins and higher protein concentration may therefore reduce denaturation. On the other hand, protein solutions comprising a high concentration of the protein of interest are in general not stable, because aggregation of said protein may occur at a faster rate (Frokjaer and Hovgaard, p. 102, Wang, 1999). To overcome the above mentioned problems it is therefore common to add stabilisers, for example protein containing stabilisers, such as albumin (Akers et al., 2000, pp. 166-167) or for example detergents to pharmaceutical formulations comprising proteins.

It is however not always desirable to add stabilisers to a pharmaceutical composition. Commonly used protein containing stabilisers such as albumin are usually purified from serum, which is undesirable because of the risk of transferring pathogens from the serum donor. In addition, it is frequently desirable to reduce the number of additives added to a pharmaceutical composition in order to keep the production as simple as possible. Fewer production steps are easier to handle, reduces costs and also reduces the risk of protein loss and degradation. Hence, it is frequently preferred that no protein stabilisers are added, for example that no protein containing stabilisers and no detergents are added.

Surprisingly, in one embodiment the present invention discloses a pharmaceutical formulations comprising MBL, wherein said pharmaceutical composition does not comprise any protein stabilisers, i.e. the formulation does not comprise other detectable protein than MBL and the formulation does not comprise any detergent.

Hence, in one preferred embodiment of the invention however, MBL essentially constitutes all of the total protein of the pharmaceutical composition. In particular, it may be preferred that the composition does not comprise proteins purified from serum or from other human or animal body samples. Because of the risk of transferring viruses or other pathogenic agents from the donor, it is frequently desirable to administer pharmaceutical compositions, which do not comprise compounds purified from serum or from other human or animal body samples.

Accordingly, in one preferred embodiment of the present invention the pharmaceutical composition does not comprise proteins or protein containing material purified from serum or from other human or animal body samples. In that embodiment it is preferred that all or essentially all protein containing material is prepared using recombinant methods.

In one embodiment of the present invention the MBL or MBL variants may be modified in order to further enhance stability. Accordingly, it is contained within the present invention that MBL or MBL variants may be PEGylated, acylated or modified in other ways to increase the half-life of MBL or MBL variants in vivo.

The term MBL and MBL variants is meant to include any form of MBL or any functional homologue thereof. In particular, MBL and MBL variants may be proteins comprising at least one polypeptide comprising the amino acid sequence identified as SEQ ID 1 or a functional homologue thereof.

MBL according to the present invention may comprise one or more subunits. Each MBL subunit normally consists of 3 individual polypeptides, preferably each individual polypeptide comprises an amino acid sequence as identified by SEQ ID 1 or a fragment thereof of a functional homologue thereof. For example MBL may be monomers, dimers, trimers, tetramers, pentamers, hexamers, heptamers, octamers, nonamers, decamers, 11-mers, 12-mers of subunits or MBL may comprise even more than 12 subunits. Preferably, MBL comprises more than two subunits.

MBL to be used with the present invention may be derived from any suitable source, for example MBL may be naturally occurring MBL or MBL may be recombinantly produced MBL. When recombinantly produced MBL is used with the present invention it is preferred that said recombinantly produced MBL has a size distribution profile that is similar to naturally occurring MBL. Accordingly, it is preferred that at least 50%, for example at least 70%, such as at least 80%, for example at least 90%, such as at least 95%, for example at least 99% MBL has a apparent molecular weight >200 kDa when determined by non-reducing SDS-PAGE.

According to the invention, MBL may be human MBL or MBL of other animal species, in which the immune system in this respect is acting like the human immune system, for example, but not limited to MBL from chimpanzees and rhesus monkeys.

In one embodiment of the present invention MBL is purified naturally occurring human serum MBL. In another embodiment of the invention MBL has been recombinantly produced. It is preferred that the MBL has been recombinantly produced.

Examples of preferred methods of producing recombinant MBL are described in PCT application WO00/70043, which is hereby incorporated herein by reference. In particular, recombinant MBL to be used in this invention may be prepared as is described in example 1 of PCT application WO00/70043. In the example the recombinant MBL is prepared by the use of an expression vector comprising sequences from the human MBL gene. MBL may also be produced as disclosed in example 1 herein below.

In order to obtain pharmaceutical compositions comprising very concentrated MBL and/or MBL variant, it may be required to concentrate an concentrated MBL and/or MBL variant composition. Concentration may be done by any conventional method, for example by using a filtration device and exposing it to a centrifugal force. However, for concentration of large protein quantities other methods may be preferred.

The invention also concerns the pharmaceutical compositions comprising MBL variants and methods using same. MBL variants may for example be functional homologues of MBL (see for example herein below). The isolated MBL peptide including any functional homologues thereof, may in one embodiment comprise at least 80 amino acid residues, such as at least 100 amino acid residues, such as at least 150 amino acid residues, such as at least 200 amino acid residues, for example at least 220 amino acid residues, such as at least 250 amino acid residues.

Other Protein

The pharmaceutical composition according to the invention may comprise other proteins than MBL.

For example the composition may comprises at least 300 µg/ml, such as at least 500 µg/ml, for example at least 750 µg/ml, such as at least 1000 µg/ml, for example at least 1300 µg/ml total protein or protein containing material. Hence, the composition may for example comprise in then range from 300 to 3000 µg/ml, such as in the range of 500 to 3000 µg/ml, for example in then range from 750 to 3000 µg/ml, such as in the range of 1000 to 3000 µg/ml, for example in then range from 1300 to 3000 µg/ml, such as in the range of 1000 to 2000 µg/ml total protein or protein containing material.

The other proteins may be any suitable proteins. In one embodiment the pharmaceutical composition may apart from MBL comprise one or more proteins naturally associated with MBL.

Hence, in one embodiment the present invention relates to a pharmaceutical composition, wherein the total protein apart from MBL furthermore comprises one or more MBL associated serine protease (MASP) or variants thereof. For example MASP and MASP variants may be selected from the group consisting of MASP-1 of SEQ ID NO: 2, MASP-2 of SEQ ID NO: 3, MASP-3 of SEQ ID NO: 4, fragments thereof and functional homologues thereof. Functional homologues of MASP proteins are described herein below.

Pharmaceutical Composition

In one aspect the present invention relates to a pharmaceutical composition. The pharmaceutical composition may be formulated in a number of different manners, depending on the purpose for the particular pharmaceutical composition.

For example the pharmaceutical composition may be formulated in a manner so it is useful for a particular administration form. Preferred administration forms are described herein below.

In one embodiment the pharmaceutical composition is formulated so it is a liquid. For example the composition may be a protein solution or the composition may be a protein suspension. Said liquid may be suitable for parenteral administration, for example for injection or infusion.

In preferred embodiments of the invention the pharmaceutical composition is suitable for bolus injection, which requires that the concentration of MBL is sufficiently high so that a suitable MBL dosage (see preferred MBL dosages herein below) may be contained in a volume, which may be administrered by bolus injection. Pharmaceutical compositions for bolus injection preferably comprises at least 500 µg/ml, more preferably at least 750 µg/ml, even more preferably at least 1000 µg/ml, for example at least 1300 µg/ml MBL and/or MBL variants.

The liquid may be any useful liquid, however it is frequently preferred that the liquid is an aqueous liquid. For many purposes, in particular when the liquid should be used for parenteral administration, it is furthermore preferred that the liquid is sterile. Sterility may be conferred by any conventional method, for example filtration, irradiation or heating.

In addition it is preferred that pharmaceutical compositions for parenteral administration have been subjected to a virus reduction step, i.e. virus filtration and/or acidic treatment. The purpose of virus filtration is a reduction of any virus contaminants. The filters used therefore are in general made of several hollow fibre membranes, where virus and other contaminants are separated from the protein solution by size exclusion. The principle behind separation is the differences between MBL and virus permeability through the hollow fibres. The difference in permeability of protein and virus is greatly increased, when the solution pass through multiple layers, hence preferably the filters used comprises several layers. Virus filtration may be performed by any conventional method known to the person skilled for example as described in example 1 herein below.

In one embodiment of the present invention the liquid may comprise one or more lipophile vehicles, for example one or more lipophile vehicle suitable for controlled release of MBL and/or MBL variants.

The liquid may furthermore contain any suitable pharmaceutically acceptable additives. Preferred pharmaceutically acceptable additives are described herein below.

For storage purposes the protein solution or protein suspension may be stored at any desirable temperature, for example from −100° C. to 0° C., such as from 0° C. to 4° C., for example from 4° C. to 10° C., such as from 10° C. to 15° C., for example from 15° C. to 25° C., such as from 15° C. to 35° C.

Accordingly, in one embodiment of the invention the solution or suspension may be frozen. For most purposes the solution or suspension is only frozen for storage purposes and must be defrozen prior to use.

The pharmaceutical composition may be packaged in single dosage units, which may be more convenient for the user. Hence, pharmaceutical compositions for bolus injections may be packages in dosage units of for example at the most 10 ml, preferably at the most 8 ml, more preferably at the most 6 ml, such as at the most 5 ml, for example at the most 4 ml, such as at the most 3 ml, for example around 2.2 ml.

The pharmaceutical composition may be packaged in any suitable container. In one example a single dosage of the pharmaceutical composition may be packaged in injection syringes.

In another embodiment of the present invention the pharmaceutical composition is a dry composition. The dry composition may be used as such, but for most purposes the composition is a dry composition for storage only. Prior to use the dry composition may be dissolved or suspended in a suitable liquid composition, for example sterile water.

Hence, the pharmaceutical composition may be a dry composition, comprising freeze-dried protein. Preferably, said dry composition is capable of being reconstituted into a solution or suspension.

The protein may be freeze-dried using any conventional method known to the person skilled in the art. For freeze drying it may be necessary to add one or more cryoprotecting agents. Examples of preferred cryoprotecting agents are given herein below.

In one embodiment of the invention the pharmaceutical composition comprises one or more further active compounds in addition to MBL and/or MBL variants. Such a pharmaceutical composition may also be provided in the form of a kit-of-parts.

Administration

The pharmaceutical composition may be prepared so it is suitable for one or more particular administration methods. Furthermore, the method of treatment described herein may involve different administration methods.

In general any administration method, wherein MBL may be administered to an individual in a manner so that active MBL may reach the site of disease may be employed with the present invention.

For example, the pharmaceutical compositions of the invention may be administered parenterally, that is by intravenous, intramuscular, subcutaneous intranasal, intrarectal, intravaginal or intraperitoneal administration. The compounds may also be administered by inhalation, that is by intranasal and oral inhalation administration. Appropriate dosage forms for such administration, such as an aerosol formulation or a metered dose inhaler, may be prepared by conventional techniques.

Accordingly, In one embodiment of the present invention the administration form may be selected from the group consisting of injection, infusion, nasal administration, transdermal administration, pulmonary administration, targeting and iontophoretic administration.

In general, for injection and infusion the pharmaceutical composition should be a sterile liquid.

Injection may be injection to any preferred site, for example injection may be selected from the group consisting of intravenous, subcutaneous, intraaterial, intramuscular and intraperitonal injection. Infusion is generally intravenous infusion.

In one preferred embodiment of the present invention the administration form is a bolus injection. For such an embodiment it is preferred that the pharmaceutical composition comprises a high concentration of MBL, so sufficient MBL may be administrated. It is an advantage of the present invention that the pharmaceutical compositions provided comprises high MBL concentrations and accordingly, allows sufficient MBL to be administrated as bolus injection.

Furthermore, the route of adminstration may be topical administration to a mucosal membrane. The mucosal membrane to which the pharmaceutical preparation of the invention is administered may be any mucosal membrane of the mammal to which the biologically active substance is to be given, e.g. in the nose, vagina, eye, mouth, genital tract, lungs, gastrointestinal tract, or rectum.

The pharmaceutical compositions according to the present invention may be administered once or more than once, for example they may be administered in the range of 2 to 5 times, such as 5 to 10 times, for example 10 to 20 times, such as 20 to 50 times, for example 50 to 100 times, such as more than 100 times.

The dosage of MBL to be administered depends on the individual to be treated as well as on the clinical condition. In general, in the range of 0.1 mg to 10 mg, such as in the range of 0.5 mg to 5 mg, for example around 1 mg MBL per 10 kg bodymass may be administered. In one embodiment of the invention the dosage is in the range of 2 to 12 mg, such as in the range of 3 to 10 mg, for example in the range of 4 to 9 mg, such as in the range of 5 to 8 mg, for example in the range of 6 to 7 mg, such as around 6.6 mg MBL per administration for an adult human being.

The pharmaceutical compositions according to the invention may be administered with at least one other active compound. The compounds may be administered simultaneously, either as separate formulations or combined in a unit dosage form, or administered sequentially.

In one embodiment of the present invention the pharmaceutical composition may be administered as part of a diagnostic procedure. For example, diagnosis may be determination of the level of one or more compounds in an individual. For diagnostic purposes it may be required to administer pharmaceutical compositions comprising high levels of MBL to said individual, for example prior to said determination.

Stability of Pharmaceutical Compositions

Preferably, the pharmaceutical formulations according to the present invention are stable, i.e. they may be long-term stored without massive loss of activity and/or without major changes in size distribution. In particular, it is preferred that MBL and/or MBL variants comprised within the pharmaceutical compositions are stable, and more preferably that MBL and/or MBL variants are stable during long-term storage.

By the term "stable" is meant, that MBL and/or MBL variants comprised within the pharmaceutical compositions preferably does maintain at least part of the initial activity during long-term storage. Hence, preferably MBL and/or MBL variants comprises at least 20%, more preferably at least 30%, even more preferably at least 40%, even more preferably at least 50%, even more preferably at least 60%, even more preferably at least 70%, even more preferably at least 80%, even more preferably at least 85%, even more preferably at least 90%, such as at least 95%, for example at least 96%, such as at least 97%, for example at least 98%, such as at least 99%, for example essentially all of the initial activity after long-term storage.

Alternatively, it is preferred that a long-term stored MBL and/or MBL variant sample comprises at least 20%, such as at least 30%, for example at least 40%, such as at least 50%, for example at least 60%, such as at least 70%, for example at least 80%, such as at least 85%, for example at least 90%, such as at least 95%, for example at least 96%, such as at least 97%, for example at least 98%, such as at least 99%, for example essentially all of the activity of an MBL sample stored at −80° C.

The activity of MBL may for example be determined by its capacity to activate or inactivate the complement system. When C4 is cleaved by MBL/MASP an active thiol ester is exposed and C4 becomes covalently attached to nearby nucleophilic groups. When an assay is performed in a coated plastic well, a substantial part of the C4b will become attached to the coated plastic well and may be detected by anti-C4 antibody. A quantitative TRIFMA for MBL activity may be performed by 1) coating microtitre wells with 1 g mannan in 100 I buffer; 2) blocking with Tween-20; 3) applying MBL complexes at a predetermined amount, applying test samples, 5) applying purified complement factor C4 at 5 g/ml; 6) incubate for one hour at 37° C.; 7) applying Eu-labelled anti-C4 antibody; 8) applying enhancement solution; and 9) reading the Eu by time resolved fluorometry. (Estimation by ELISA may be carried out similarly, e.g. by applying biotin-labelled anti-C4 in step 7; 8) apply alkaline phosphatase-labelled avidin; 9) apply substrate; and 10) read the colour intensity). Between each step the plate was incubated at room temperature and washed, except between step 8 and 9. A calibration curve can be constructed using dilutions of MBL with known activity. The assay is preferably carried out at conditions which preclude activation of C4 by the classical or alternative complement activation pathways. The activation of C4 was completely inhibited by the serine protease inhibitor benzamidine. Activation of the classical pathway is effectively eliminated by carrying out step 3) in the presence of sufficiently high ionic strength (0.7 to 2.0 MNaCl; preferably about 1.0 M NaCl) which does not interfere with the MBL complex but comletely destroys the C1qrs complex; activation of the alternative pathway is effectively precluded by assaying at dilution as described above.

It is however preferred that the activity of MBL is determined according to the C4 activation assay described in example 9 herein below.

Preferably, stable MBL and/or MBL variants are not broken down or only broken down in a limited amount during long-term storage, i.e. preferably stable MBL and/or MBL variants are not broken down or only broken down in a limited amount by either physically and/or chemical break down during storage. Accordingly, preferably the majority of polypeptides comprised within the MBL and/or MBL variants are of the same length (i.e. are containing the same amount of amino acids) after storage as before storage. The lengths of MBL and/or MBL variants and the amino acid content as well as MBL protein concentration may be determined by a number of different methods, for example by amino acid analysis, anion exchange chromatography, by coomasie staining on reduced MBL or by non-reduced MBL western blots, by mass spectrometry or by size exclusion chromatography.

Hence, preferably at least 10%, such as at least 20%, such as at least 30%, for example at least 40%, such as at least 50%, for example at least 60%, such as at least 70%, for example at least 80%, such as at least 85%, for example at least 90%, such as at least 95%, for example at least 96%, such as at least 97%, for example at least 98%, such as at least 99% of the MBUMBL variant polypeptides are at least 50%, for example at least 60%, such as at least 70%, for example at least 80%, such as at least 85%, for example at least 90%, such as at least 95%, for example at least 96%, such as at least 97%, for example at least 98%, such as at least 99%, for example around 100% of the initial length.

Furthermore, it is preferred that at least 50%, for example at least 60%, such as at least 70%, for example at least 80%, such as at least 85%, for example at least 90%, such as at least 95%, for example at least 96%, such as at least 97%, for example at least 98%, such as at least 99% of the MBL/MBL variant polypeptides show no changes in the polypeptide chain after storage when investigated by mass spectrometry.

In addition it is preferred that at least 50%, for example at least 60%, such as at least 70%, for example at least 80%, such as at least 85%, for example at least 90%, such as at least 95%, for example at least 96%, such as at least 97%, for example at least 98%, such as at least 99% of the stored MBL/MBL variant polypeptides eluates similar to initial MBL/MBL variants or MBL/MBL variants stored at −80° C. after size exclusion chromatography. Size exclusion chromatography may for example be performed as described in example 10 herein below.

By the term "initial length" is meant the length of MBL/MBL variant polypeptides before storage or alternatively the length of MBL/MBL variant polypeptides stored at −80° C., which in one preferred embodiment of the invention corresponds to full length MBL, for example the full length of the polypeptide as identified by SEQ ID NO. 1. In general the length of MBUMBL variant may be determined by determining the molecular weight of MBUMBL variant polypeptides as measured in Daltons.

By the term long-term storage is meant storage for in the range of 1 to 4 weeks, such as 1 to 3 months, such as 3 to 6 months, such as 6 to 12 months, for example 1 to 2 years, such as 2 to 3 years, for example 3 to 5 years, such as 5 to 7 years, for example 7 to 10 years, such as more than 10 years. Preferably, long-term storage is in the range of 1 to 2 years, more preferably in the range of 2 to 5 years.

The stability of MBL and/or MBL variants is dependent on the storage conditions. Preferably, MBL and/or MBL variants are stable when stored at a temperature for example in the range of −80° C. to −20° C., such as −25° C. to −15° C., for example −15° C. to 0° C., such as 0° C. to 4° C., for example 2° C. to 10° C., such as 5° C. to 15° C., for example −10° C. to 20° C., such as 15° C. to 35° C., for example 15° C. to 30° C., such as 15° C. to 25° C. In one preferred embodiment of the invention MBL and/or MBL variants may be stored at temperatures around 4° C., in another preferred embodiment of the invention MBL and/or MBL variants may be stored at temperatures around −20° C., in yet another preferred embodiment of the invention MBL and/or MBL variants may be stored at temperatures around 37° C.

The stability of MBL and/or MBL variants may furthermore be dependent on the nature of the pharmaceutical composition. For example, the stability of MBL and/or MBL variants may be different when the pharmaceutical composition is a solution, a suspension or dry matter.

Functional Homologues

Functional homologues of polypeptides according to the present invention is meant to comprise any polypeptide sequence which is capable of performing essentially the same function or partially the same function as a polypeptide of a specific predetermined sequence.

Accordingly, functional homologues according to the present invention comprise polypeptides with an amino acid sequence, which are sharing at least some homology with a predetermined polypeptide sequences as outlined herein above.

Preferably, functional homologues of human MBL comprises polypeptides which share at least some homology with the polypeptides as identified by SEQ ID NO 1. Preferably, functional homologues of human MASP-1 comprises polypeptides which share at least some homology with the polypeptides as identified by SEQ ID NO 2. Preferably, functional homologues of human MASP-2 comprises polypeptides which share at least some homology with the polypeptides as identified by SEQ ID NO 3. Preferably, functional homologues of human MASP-3 comprises polypeptides which share at least some homology with the polypeptides as identified by SEQ ID NO 4.

For example such polypeptides are at least about 40 percent, such as at least about 50 percent homologous, for example at least about 60 percent homologous, such as at least about 70 percent homologous, for example at least about 75 percent homologous, such as at least about 80 percent homologous, for example at least about 85 percent homologous, such as at least about 90 percent homologous, for example at least 92 percent homologous, such as at least 94 percent homologous, for example at least 95 percent homologous, such as at least 96 percent homologous, for example at least 97 percent homologous, such as at least 98 percent homologous, for example at least 99 percent homologous with the predetermined polypeptide sequences as outlined herein above.

Homology may preferably be calculated by any suitable algorithm or by computerised implementations of such algorithms for example CLUSTAL in the PC/Gene program by Intelligenetics or GAP, BESTFIT, BLAST, FASTA and TFASTA in the Wisconsin Genetics Software Package, Genetics Computer Group (GCG). The homology between amino acid sequences may furthermore be calculated with the aid of well known matrices such as for example any one of BLOSUM 30, BLOSUM 40, BLOSUM 45, BLOSUM 50, BLOSUM 55, BLOSUM 60, BLOSUM 62, BLOSUM 65, BLOSUM 70, BLOSUM 75, BLOSUM 80, BLOSUM 85, and BLOSUM 90.

Functional homologues may comprise an amino acid sequence that comprises at least one substitution of one amino acid for any other amino acid. For example such a substitution may be a conservative amino acid substitution or it may be a non-conservative substitution.

A conservative amino acid substitution is a substitution of one amino acid within a predetermined group of amino acids for another amino acid within the same group, wherein the amino acids within a predetermined groups exhibit similar or substantially similar characteristics. Within the meaning of the term "conservative amino acid substitution" as applied herein, one amino acid may be substituted for another within groups of amino acids characterised by having i) polar side chains (Asp, Glu, Lys, Arg, His, Asn, Gln, Ser, Thr, Tyr, and Cys,)

ii) non-polar side chains (Gly, Ala, Val, Leu, lIe, Phe, Trp, Pro, and Met)

iii) aliphatic side chains (Gly, Ala Val, Leu, Ile)

-continued iv) cyclic side chains (Phe, Tyr, Trp, His, Pro)

v) aromatic side chains (Phe, Tyr, Trp)

vi) acidic side chains (Asp, Glu)

vii) basic side chains (Lys, Arg, His)

viii) amide side chains (Asn, Gln)

ix) hydroxy side chains (Ser, Thr)

x) sulphor-containing side chains (Cys, Met), and xi) amino acids being monoamino-dicarboxylic acids or monoamino-monocarboxylic-monoamidocarbosylic acids (Asp, Glu, Asn, Gln).

Functional homologues according to the present invention may comprise more than one such substitution, such as e.g. two amino acid substitutions, for example three or four amino acid substitutions, such as five or six amino acid substitutions, for example seven or eight amino acid substitutions, such as from 10 to 15 amino acid substitutions, for example from 15 to 25 amino acid substitution, such as from 25 to 30 amino acid substitutions, for example from 30 to 40 amino acid substitution, such as from 40 to 50 amino acid substitutions, for example from 50 to 75 amino acid substitution, such as from 75 to 100 amino acid substitutions, for example more than 100 amino acid substitutions.

The addition or deletion of an amino acid may be an addition or deletion of from 2 to 5 amino acids, such as from 5 to 10 amino acids, for example from 10 to 20 amino acids, such as from 20 to 50 amino acids. However, additions or deletions of more than 50 amino acids, such as additions from 50 to 200 amino acids, are also comprised within the present invention.

The polypeptides according to the present invention, including any variants and functional homologues thereof, may in one embodiment comprise more than 5 amino acid residues, such as more than 10 amino acid residues, for example more than 20 amino acid residues, such as more than 25 amino acid residues, for example more than 50 amino acid residues, such as more than 75 amino acid residues, for example more than 100 amino acid residues, such as more than 150 amino acid residues, for example more than 200 amino acid residues.

Additional factors may be taken into consideration when determining functional homologues according to the meaning used herein. For example functional homologues may be capable of associating with antisera which are specific for the polypeptides according to the present invention.

Peptides with N-terminal alkylations and C-terminal esterifications are also encompassed within the present invention. Functional homologues also comprise post-translationally modified polypeptides, for example glycosylated polypeptides.

Pharmaceutically Acceptable Additives

The pharmaceutical compositions containing MBL or MBL variants may be prepared by any conventional technique, e.g. as described in Remington: The Science and Practice of Pharmacy 1995, edited by E. W. Martin, Mack Publishing Company, 19th edition, Easton, Pa.

The pharmaceutical acceptable additives may be any conventionally used pharmaceutical acceptable additive, which should be selected according to the specific formulation, intended administration route etc. For example the pharmaceutical acceptable additives may be any of the additives mentioned in Nema et al, 1997. Furthermore, the pharmaceutical acceptable additive may be any accepted additive from FDA's "inactive ingredients list", which for example is available on the internet address http://www.fda.gov/cder/drug/iig/default.htm.

In some embodiments of the present invention it is desirable that the pharmaceutical composition comprises an isotonic agent. In particular when the pharmaceutical composition is prepared for administration by injection or infusion it is often desirable that an isotonic agent is added.

Accordingly, the composition may comprise at least one pharmaceutically acceptable additive which is an isotonic agent.

The pharmaceutical composition may be isotonic, hypotonic or hypertonic. However it is often preferred that a pharmaceutical composition for infusion or injection is essentially isotonic, when it is administrated. Hence, for storage the pharmaceutical composition may preferably be isotonic or hypertonic. If the pharmaceutical composition is hypertonic for storage, it may be diluted to become an isotonic solution prior to administration.

The isotonic agent may be a ionic isotonic agent such as a salt or a non-ionic isotonic agent such as a carbohydrate.

Examples of ionic isotonic agents include but are not limited to NaCl, $CaCl_2$, KCl and $MgCl_2$ Examples of non-ionic isotonic agents include but are not limited to mannitol and glycerol.

It is also contained within the present invention that at least one pharmaceutically acceptable additive is a buffer. For some purposes, for example, when the pharmaceutical composition is meant for infusion or injection, it is often desirable that the composition comprises a buffer, which is capable of buffering a solution to a pH in the range of 4 to 10, such as 5 to 9, for example 6 to 8.

However, in other embodiments of the invention the pharmaceutical composition may comprise no buffer at all or only micromolar amounts of buffer.

The buffer may for example be selected from the group consisting of TRIS, acetate, glutamate, lactate, maleate, tartrate, phosphate, citrate, carbonate, glycinate, histidine, glycine, succinate and triethanolamine buffer. Hence, the buffer may be $K_2HPO_4$, $Na_2HPO_4$ or sodium citrate.

TRIS buffer is known under various other names for example tromethamine including tromethamine USP, THAM, Trizma, Trisamine, Tris amino and trometamol. The designation TRIS covers all the aforementioned designations.

The buffer may furthermore for example be selected from USP compatible buffers for parenteral use, in particular, when the pharmaceutical formulation is for parenteral use. For example the buffer may be selected from the group consisting of monobasic acids such as acetic, benzoic, gluconic, glyceric and lactic, dibasic acids such as aconitic, adipic, ascorbic, carbonic, glutamic, malic, succinic and tartaric, polybasic acids such as citric and phosphoric and bases such as ammonia, diethanolamine, glycine, triethanolamine, and TRIS.

In preferred embodiments of the present invention, the pharmaceutical compositions according to the present invention do not contain stabilisers, in particular it is preferred that the pharmaceutical compositions do not contain protein containing stabilisers, even more preferably the pharmaceutical compositions do not contain protein containing stabilisers and detergents. Pharmaceutical formulations wherein the active ingredient is a protein or a peptide in general comprise one or more stabilisers. Said stabilisers are frequently one or more proteins or one or more detergents. It is frequently desirable to reduce the amount of additives in a pharmaceutical composition. Hence, preferred pharmaceutical compositions according to the present invention do not contain any protein and/or detergent.

However, in other embodiments of the invention pharmaceutical compositions, may comprise at least one pharmaceutically acceptable additive which is a stabiliser. The stabiliser may for example be a detergent, an amino acid, a fatty acid, a polymer, a polyhydric alcohol, a metal ion, a reducing agent, a chelating agent or an antioxidant, however any other suitable stabiliser may also be used with the present invention.

For example the stabiliser may be selected from the group consisting of poloxamers, Tween-20, Tween-40, Tween-60, Tween-80, Brij, metal ions, amino acids, polyethylene glucol, Triton, EDTA and ascorbic acid.

Furthermore, the stabiliser may be selected from the group consisting of amino acids such as glycine, alanine, arginine, leucine, glutamic acid and aspartic acid, surfactants such as polysorbate 20, polysorbate 80 and poloxamer 407, fatty acids such as phosphotidyl cholinem ethanolamine and acethyltryptophanate, polymers such as polyethylene glycol and polyvinylpyrrolidone, polyhydric alcohol such as sorbitol, mannitol, glycerin, sucorse, glucose, propylene glycol, ethylene glycol, lactose and trehalose, antioxidants such as ascorbic acid, cysteine HCL, thioglycerol, thioglycolic acid, thiosorbitol and glutathione, reducing agents such as several thiols, chelating agents such as EDTA salts, gluthamic acid and aspartic acid and metal ions such as $Ca^{++}$, $Ni^{++}$, $Mg^{++}$ and $Mn^{++}$.

Other examples of antioxidants and reducing agents useful with the present invention includes acetone sodium bisulfite, ascorbate, bisulfite sodium, butylated hydroxy anisole, butylated hydroxy toluene, cystein/cysteinate HCL, dithionite sodium, gentisic acid, gentisic acid ethanolamine, glutamate monosodium, formaldehyde sulfoxylate sodium, metabisulfite potassium, metabisulfite sodium, monothioglycerol, propyl gallate, sulfite sodium and thioglycolate sodium.

The pharmaceutical composition according to the invention may also comprise one or more cryoprotectant agents. In particular, when the composition comprises freeze-dried protein or the composition should be stored frozen it may be desirable to add a cryoprotecting agent to the pharmaceutical composition.

The cryoprotectant agent may be any useful cryoprotectant agent, for example the cryoprotectant agent may be selected from the group consisting of dextran, glycerin, polyethylenglycol, sucrose, trehalose and mannitol.

Accordingly, the pharmaceutically acceptable additives may comprise one or more selected from the group consisting of isotonic salt, hypertonic salt, buffer and stabilisers. Furthermore, the pharmaceutically acceptable additives may comprise one or more selected from the group consisting of isotonic agents, buffer, stabilisers and cryoprotectant agents. For example, the pharmaceutically acceptable additives comprise glucosemonohydrate, glycine, NaCl and polyethyleneglycol 3350.

In another aspect the invention relates to an MBL composition comprising one or more cations.

Surprisingly, the addition of cations to an MBL solution may result in an increased stability of MBL and/or MBL variants. Preferably, the compositions comprises in the range of 0.01 mM to 1000 mM, more preferably in the range of 0.05 mM to 500 mM, even more preferably in the range of 0.1 mM to 100 mM, yet more preferably in the range of 0.2 mM to 50 mM, even more preferably in the range of 0.3 mM to 25 mM, yet more preferably in the range of 0.5 mM to 10 mM, such as in the range of 0.5 mM to 5 mM, for example in the range of 0.5 mM to 2 mM, such as around 1 mM divalent cation. The cation is preferably a divalent cation, and accordingly the invention relates to an MBL composition comprising one or more divalent cations.

The divalent cation is preferably a metal divalent cationic. For example the divalent cation may be selected from the group consisting of $Ca^{++}$, $Ni^{++}$, $Mg^{++}$ and $Mn^{++}$. Preferably, however the divalent cation is $Ca^{++}$. $Ca^{++}$ may be added to the solution as any suitable salt, for example as $CaCl_2$.

In a preferred embodiment the MBL composition is as described above with respect to MBL content.

Clinical Condition

A number of clinical conditions may be treated using the pharmaceutical compositions according to the present invention. In particular however the following conditions may be treated:

1. Infections
2. MBL deficiency
3. Immunocompromised conditions

Infections may for example be an infection by bacteria, fungi, viruses, parasites. For example infection by one or more bacteria selected from the group consisting of *Achromobacter xylosoxidans*, *Acinetobacter calcoaceticus*, preferably *A. anitratus*, *A. haemolyticus*, *A. alcaligenes*, and *A. Iwoffii*, *Actinomyces israelii*, *Aeromonas hydrophilia*, Alcaligenes species, preferably *A. faecalis*, *A. odorans* and *A. denitrificans*, *Arizona hinshawii*, *Bacillus anthracis*, *Bacillus cereus*, *Bacteroides fragilis*, *Bacteroides melaninogenicus*, *Bordetella pertussis*, *Borrelia burgdorferi*, *Borrelia recurrentis*, Brucella species, preferably *B. abortus*, *B. suis*, *B. melitensis* and *B. canis*, *Calymmatobacterium granulomatis*, *Campylobacter fetus* ssp. intestinal is, *Campylobacter fetus* ssp. jejuni, Chlamydia species, preferably *C. psittaci* and *C. trachomatis*, *Chromobacterium violaceum*, Citrobacter species, preferably *C. freundii* and *C. diversus*, *Clostridium botulinum*, *Clostridium perfringens*, *Clostridium difficile*, *Clostridium tetani*, *Corynebacterium diphtheriae*, Corynebacterium, preferably *C. ulcerans*, *C. haemolyticum* and *C. pseudotuberculosis*, *Coxiella bumetii*, *Edwardsiella tarda*, *Eikenella corrodens*, Enterobacter, preferably *E. cloacae*, *E. aerogenes*, *E. hafniae* (also named *Hafnia alvei*) and *E. agglomerans*, *Erysipelothrix rhusiopathiae*, *Escherichia coli*, *Flavobacterium meningosepticum*, *Francisella tularensis*, *Fusobacterium nucleatum*, *Gardnerella vaginalis*, *Haemophilus ducreyi*, *Haemophilus influenzae*, Helicobacter species, Klebsiella species, preferably *K. pneumoniae*, *K. ozaenae* og *K. rhinoscleromatis*, Legionella species, *Leptospira interrogans*, *Listeria monocytogenes*, Moraxella species, preferably *M. lacunata* and *M. osloensis*, Mycobacteri-

*oum bovis*, *Mycobacterium leprae*, *Mycobacterium tuberculosis*, Mycoplasma species, preferably *M. pneumoniae*, *Neisseria gonorrhoeae*, *Neisseria meningitidis*, Nocardia species, preferably *N. asteroides* and *N. brasiliensis*, *Pasterurella haemolytica*, *Pasteurella multocida*, *Peptococcus magnus*, *Plesiomonas shigelloides*, Pneumococci, Proteus species, preferably *P. mirabilis*, *P. vulgaris*, *P. rettgeri* and *P. morganii* (also named *Providencia rettgeri* and *Morganella morganii* respectively), Providencia species, preferably *P. alcalifaciens*, *P. stuartii* and *P. rettgeri* (also named *Proteus rettgeri*), *Pseudomonas aeruginosa*, *Pseudomonas mallei*, *Pseudomonas pseudomallei*, Rickettsia, *Rochalimaia henselae*, Salmonella species, preferably *S. enteridis*, *S. typhi* and *S. derby*, and most preferably Salmonella species of the type Salmonella DT104, Serratia species, preferably *S. marcescens*, *Shigella dysenteriae*, *S. flexneri*, *S. boydii* and *S. sonnei*, *Spirillum minor*, *Staphylococcus aureus*, *Staphylococcus epidermidis*, *Staphylococcus saprophyticus*, *Streptobacillus moniliformis*, Streptococcus, preferably *S. faecalis*, *S. faecium* and *S. durans*, *Streptococcus agalactiae*, *Streptococcus pneumoniae*, *Streptococcus pyogenes*, *Treponema carateum*, *Treponeam pailidum*, *Treponema pertenue*, preferably *T. pallidum*, *Ureaplasma urealyticum*, *Vibrio cholerae*, *Vibrio parahaemolyticus*, *Yersinia enterocolitica*, and *Yersinia pestis*.

Immuno compromised conditions includes any functional deficiency of one or more components of the immune system, for example one or more components of the cellular immune system, such as for example immune cells or one or more components of the humoral immune system. The deficiency may be caused by lack of the component or by the presence of reduced amounts of the component or may be due to functional alterations of the component or parts of the component.

In one example the immunocompromised condition may be MASP deficiency.

Individual in Need of MBL Treatment

The individual in need of MBL treatment or a medicament comprising MBL according to the invention may be any individual, for example it may be an individual suffering from a clinical condition or an individual in risk of acquiring a clinical condition. Preferably, the individual is a human being.

In a preferred embodiment of the present invention, the individual is suffering from one of the clinical conditions described herein above. In another preferred embodiment the individual is at increased risk of acquiring a clinical condition as described herein above.

For example the individual may have increased risk of acquiring an infection. The increased risk may have several different reasons, however frequently the increased risk will be associated with a functional deficiency in one or more components of the immune system. The functional deficiency of the immune system may be a deficiency in the cellular immune system and//or the humoral immune system.

Components of the cellular immune systems involves for example neutrophiles, T-cells, B-cells, basophiles and phagocytes. The functional deficiency may be coursed by a reduced number of one or more of said cells or by malfunction of one or more of said cells.

Components of the humoral immune systems includes for example the complement pathway and the lectin complement pathway. Accordingly, in one embodiment of the invention, the individual is an individual with a functional deficiency of MBL. For example the individual may have a subnormal serum level of MBL.

A subnormal MBL serum level refers to a concentration of MBL in serum, which is lower than the normal serum concentration of MBL. For example the MBL serum level may be <2000 ng/ml, such as <1500 ng/ml, for example <1000 ng/ml, such as <900 ng/ml, for example <800 ng/ml, such as <700 ng/ml, for example <600 ng/ml, such as <500 ng/ml, for example <400 ng/ml, such as <300 ng/ml, for example <200 ng/ml, such as <100 ng/ml.

EXAMPLES

The following examples illustrate selected embodiments of the present invention and should not be regarded as limiting for the invention.

Example 1

| MBL formulation | |
| --- | --- |
| Content | Concentration |
| MBL | 1 mg/ml |
| Tris-buffer | 10 mM, pH 7,4 |
| NaCl | 140 mM |

MBL is recombinant human MBL prepared and purified as described in PCT application WO00/70043. Briefly, the genomic human MBL gene was amplified by PCR and inserted into a pREP9 vector (cat.no. V009-50, Invitrogen). HEK 293EBNA cells were transfected with the contruct and culture medium from the MBL/pREP9 transfected cells, was passed over a column of Fractogel TSK HW-75 beads (cat.no. 14985, Merck KgaA, Darmstadt, Germany), which had been coupled to mannose and been pre-washed in 15 mL of 0.1 M glycin (pH 3.0) and equilibrated in TBS/0.05% (v/v) Tween-20, 2 mM $CaCl_2$. The column was washed in 75 mL of TBS, 2 mM $CaCl_2$.

Recombinant MBL is eluated in a buffer containing 10 mM Tris-buffer and 140 mM NaCl in the last purification step. Subsequently, the formulation is virus filtered over a Planova filter consisting of 150 layers, which leads to high virus retention (7 logs).

Several Planova filters exist and the filters of size 75N and 35N are selected for virus filtration of MBL solution. The 75N and 35N were selected after a study of the MBL recovery using Planova filters with different pore size. Filters 15N and 20N are commercial avaible but the pore size is too small for filtrating MBL. The 75N filter will only filter larger virus like HIV and operate more as a prefilter than a virus removal filter. The Planova 35N will remove virus larger than 35 nm size, which include reovirus but not smaller vira like polio- and parvovirus. For smaller virus, an acidic treatment step during MBL purification is assumed to be effective for virus inactivation.

First, the MBL solution is passed through the 75N filter and secondly the filtrate is thereafter passed through the 35N filter. Both filtrations are carried out as dead end filtration. For laboratory scale a 0.01 $m^2$ filter is used. In pilot production scale, a filter of 0.3 $m^2$ is used.

Finally, the MBL solution is diluted in 10 mM Tris-buffer and 140 mM NaCl to a final concentration of 1 mg/ml, sterile filtered over a 0.22 μm filter and aliquoted into 2.2 ml aliqouts.

This formulation is suitable for parenteral administration. In particular, 1 aliquot may be administered to a human child (depending on age) and 3 aliquots may be administered to a human adult.

Example 2

| MBL formulation | |
|---|---|
| Content | In 1 ml of the formulation: |
| MBL | 1 mg |
| Tris-buffer | 1.2 mg |
| NaCl | 5.8 mg |
| Mannitol | 7.3 mg |

MBL is recombinant human MBL prepared and purified as described in PCT application WO00/70043. Recombinant MBL is eluated in a buffer containing 1.2 mg/ml Tris-buffer and 5.8 mg/ml NaCl in the last purification step. Subsequently, 7.3 mg/ml mannitol is added to the MBL solution. The formulation is sterile filtered prior to use.

This formulation is suitable for parenteral administration.

Example 3

| MBL formutation | |
|---|---|
| Content | In 1 ml of the formulation: |
| MBL | 1 mg |
| Tris-buffer | 1.2 mg |
| NaCl | 5.8 mg |
| Mannitol | 7.3 mg |
| Tween-80 | 0.1 mg |

MBL is recombinant human MBL prepared and purified as described in PCT application WO00/70043. Recombinant MBL is eluated in a buffer containing 1.2 mg/ml Tris-buffer and 5.8 mg/ml NaCl in the last purification step. Subsequently, 7.3 mg/ml mannitol and 0.1 mg Tween-80 is added to the MBL solution. The formulation is steril filtered and virus filtered (see example 1) prior to use.

This formulation is suitable for parenteral administration.

Example 4

MBL formulation
  10 mg/ml MBL
  10 mM tris, pH=7.4.
  140 mM NaCl

Recombinant MBL is prepared as described in example 1. MBL is then concentrated using a filtration device exposing the protein to 3500× G. The formulation is sterile filtered and virus filtered (see example 1) prior to use.

The formulation is suitable for parenteral administration.

Example 5:

MBL: 1 mg/ml
Trisbuffer: 10 mM
NaCl: 140 mM
$CaCl_2$: 0.1 mM

Recombinant MBL is prepared as described in example 1. $CaCl_2$ is added to a final concentration of 1 mM. The formulation is sterile filtered and virus filtered (see example 1) prior to use.

The formulation is suitable for parenteral administration.

Example 6:

MBL: 5 mg/ml
Trisbuffer: 10 mM
NaCl: 140 mM
$CaCl_2$: 1 mM

Recombinant MBL is prepared as described in example 1. MBL is then concentrated using a filtration device exposing the protein to 3500× G. $CaCl_2$ is added to a final concentration of 1 mM. The formulation is sterile filtered and virus filtered (see example 1) prior to use.

The formulation is suitable for parenteral administration.

Example 7

MBL: 10 mg/ml
Trisbuffer: 10 mM
NaCl: 140 mM
$CaCl_2$: 1 mM

Recombinant MBL is prepared as described in example 1. MBL is then concentrated using a filtration device exposing the protein to 3500× G. $CaCl_2$ is added to a final concentration of 1 mM. The formulation is sterile filtered and virus filtered (see example 1) prior to use.

The formulation is suitable for parenteral administration.

Example 8

Stability of Pharmaceutical Formulations Comprising MBL

Recombinant MBL has been formulated as a liquid solution, and stability tested in storage material acceptable for liquid protein storage. A number of three different formulations with different concentrations of MBL were tested and one formulation was tested for a stabilizing effect of calcium ions.

A formulation on 1 mg/ml without any protein stabilizing excipients showed surprisingly high stability when stored frozen (−20° C.) and chilled (+4° C.) for 12 months. No activity decrease was measured nor were changes in the polypeptide chain when investigated by mass spectrometry. No changes were observed in protein content by amino acid analysis or anion exchange chromatography. No degradation products were observed by coomasie staining on reduced MBL or by non-reduced MBL western blots. A small front peak, which probably is caused by aggregated MBL, corresponding to only approximately 1% of total MBL content was observed by size exclusion chromatography. Results obtained for a higher MBL formulation (10 mg/ml and 5 mg/ml) indicate the possibility of aggregate formation caused by the stressful concentration step rather than by storage. Addition of calcium ions showed dramatically stabilizing effect with no changes in activity after 2 months of storage at +37° C.

Introduction

Three pharmaceutical formulations comprising recombinant mannose binding lectin (rMBL) have been developed and filled into storage material acceptable for pharmaceutical use. Filling was done aseptically using only sterile vials, rubber stoppers and performed in a laminar air hood. Type of formulation, storage material and filling process therefore make the preparation highly representative of a MBL drug product for clinical use. These formulations were stability tested by storage at different temperatures and incubation time. Storage equipment were all temperature monitorated.

The following MBL formulations were studied:

PE0238: 1 mg/ml MBL in 10 mM tris,140 mM NaCl and pH=7.4.

PE0305: 10 mg/ml MBL in 10 mM tris, 140 mM NaCl and pH=7.4.

PE0407: 5 mg/ml MBL in 10 mM tris,140 mM NaCl, 1 mM $CaCl_2$ and pH=7.4.

All references used in these studies are kept at −80° C. and accepted as stable when used.

Methods

The C4-Activation Assay

C4 activation assay was performed as described in example 9 herein below. The C4 activation assay measures the capability of MBL to bind to MASPs (mannose binding protein associated proteases), and upon binding to a carbohydrate target, activate the MASPs. The MBL/MASP complex subsequently cleaves C4 and initiates the lectin pathway of complement activation. C4 activation is therefore a measure of the biological potency of MBL.

This assay is the major stability-indicating assay for MBL.

Size Exclusion Chromatography (SEC)

SEC is a chromatographic analysis performed on a Superose 6 column (Amersham Biosciences) as described in example 10 herein below; MBL and other components are separated by molecular volume, which for globular proteins is proportional to molecular mass.

The SEC analysis is used for verification of the high-mass structure of MBL. While high-mass oligomers elute early in a chromatogram, non-oligomers elute late in the chromatogram. Moreover, aggregates larger than oligomeric MBL can be detected, if present in the sample. Finally, the analysis might also be used for quantifying MBL content.

Mass Spectrometry (MALDI-MS)

Initially, the sample is reduced and purified according to a generic procedure to remove non-protein components and limit background signal. MALDI-MS is done to verify the mass profile of the MBL polypeptide chain and to identify potential degradation products of the polypeptide chain.

Results

C4-Activation Assay

Figure 1:
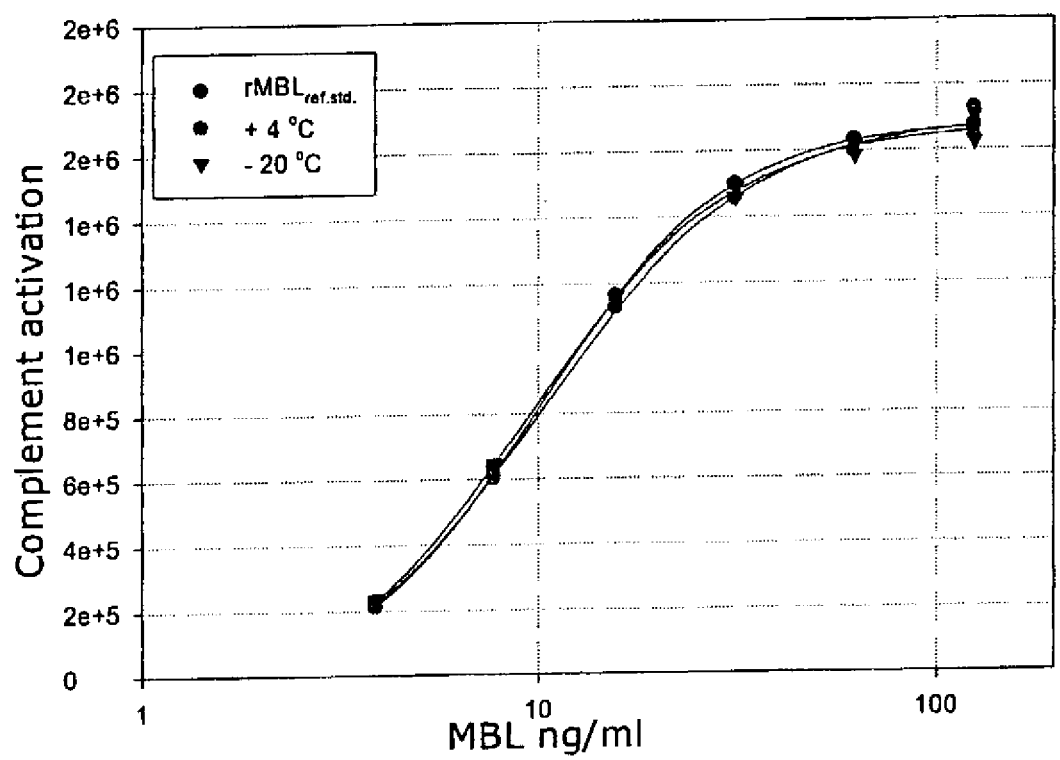
FIG. 1 illustrates the C4 activation data for 1 mg/ml MBL formulation samples stored 12 months at +4 and −20 compared to the reference MBL.

PE0238: The C4-activation assay indicate identical activity for the 1 mg/ml formulation, when stored 12 months at −20 and +4 degree C. as for the reference. Results are shown in FIG. 1 as a six-point curve with EC50 values at 105% for +4 degree storage and 104% for −20 degree storage compared to the reference at 100%.

PE0305: The initial activity is measured to 94% relative to the standard reference for the 10 mg/ml formulation. After 2½ months the activity is decreased to around 80% for the frozen and chilled samples and to 36% for the +37 degree sample. After 5 months the activity is still around 80% for frozen and chilled samples, where a drop to 14.3% is measured for the +37° C. sample. Results are obtained by C4-activation stability curves and listed as EC50 values in table 1. Only changes of more than −15 % are considered as significant.

TABLE 1

C4-activation on stability samples.

| Type of storage | −20° C. | +4° C. | +37° C. |
|---|---|---|---|
| T = 0 months | 94% (N = 1) | Same as −20° C. | Same as −20° C. |
| T = 2½ months | 81% (N = 1) | 78% (N = 1) | 36% (N = 1) |
| T = 5 months | 81.7% ± 4.7 (N = 3) | 80.3% ± 7.6 (N = 3) | 14.3% ± 1.5 (N = 3) |

The T = 0 analyse is a single estimation. Activity is calculated in EC50% relative to a MBL standard. Measurements in triplicate are illustrated with standard variations.

PE0407: The 5 mg/ml formulation was activity tested and surprisingly is only a very small activity decrease observed for the sample stored at +37 degree and compared to the frozen sample are no changes observed. Activities are measured to 91% for the frozen, 92 for the chilled sample and 94 for the sample at +37 degree C. A control without calcium was incubated at +37 degree and measured to 19% activity. Results are obtained by C4-activation curves and listed in table 2 as EC50 values.

TABLE 2

C4-activation data on 5 mg/ml stability samples compared to the reference N105-11A, EC50 = 100%.

| Type of storage | −20° C. | +4° C. | +37° C. | Control 37° C. |
|---|---|---|---|---|
| T = 2 months | 91% | 92% | 94% | 19% |

SEC Data.

Figure 2:
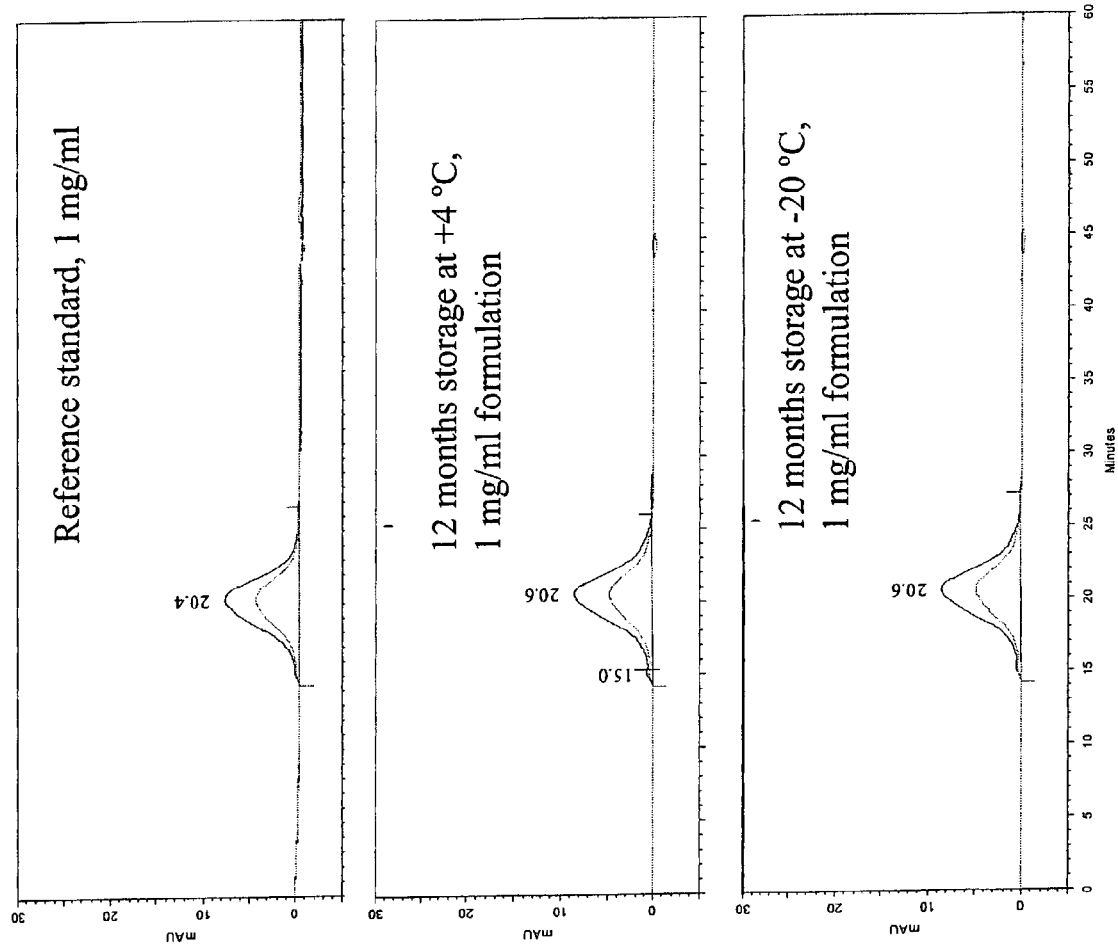
FIG. 2 illustrates the SEC chromatograms of the reference standard in top followed by 1 mg/ml stability sample kept at +4 degree and at −20 degree. A small front peak is detected in the sample kept chilled corresponding to 1% of the total MBL content.

PE0238: The 1 mg/ml formulation was analysed for detecting molecular mass changes. The reference elute at 20.4 minutes as a single peak. For chilled storage a small front peak is eluting at 15 minutes, the front peak corresponds to approximately 1% of total MBL content. For frozen storage the peak is identical to the reference with no detection of front peak. FIG. 2 illustrates the SEC chromatograms of the reference standard in top followed by 1 mg/ml stability sample kept at +4 degree and at −20 degree. A small front peak is detected in the sample kept chilled corresponding to 1% of the total MBL content.

PE305: SEC data from the 10 mg/ml formulation indicate generation of a front peak. The amount of MBL in the front peak is calculated by comparison to the total MBL content and illustrated in table 3 as front peak in % of total MBL. According to table 3 are front peaks detected in all samples corresponding to 3 to 5% of total MBL for storage at frozen and chilled temperatures. At +37 degree 40% is observed after 2½ months and 56% is present in the front peak after 5 months of storage.

TABLE 3

The amount of MBL present in the front peak in % of total MBL. All measurements are in duplicate.

| Type of storage | −20° C. | +4° C. | +37° C. |
|---|---|---|---|
| T = 2½ months | 3.5% ± 1.6 (N = 2) | 5.3% ± 0.1 (N = 2) | 39.5% ± 3.0 (N = 2) |
| T = 5 months | 4.1% ± 1.6 (N = 2) | 3.4% ± 2.1 (N = 2) | 56.5% ± 16.1 (N = 2) |

PE0407: Front peaks are observed in the 5 mg/ml formulation with amounts between 1 and 3%. A control without calcium and incubated at +37 degree was the MBL content in front peak measured to 62%.

TABLE 4

The amount of MBL present in the front peak in % of total MBL.
All measurements are single estimations

| Type of storage | −20° C. | +4° C. | +37° C. | Control 37° C. |
|---|---|---|---|---|
| T = 2 months | 2% (N = 1) | 1% (N = 1) | 3% (N = 1) | 62% (N = 1) |

MS Data

PE238: Mass spectrometry analyses on reduced MBL indicate an intact MBL poly-peptide chain during 12 months of storage at −20 and +4 degree, nor are changes observed after 6 months of storage at +37 degree. MS spectrograms are illustrated in FIG. 3.

MBL does not appear as a single peak due to different hydroxylation and glycolysation profiles, normally resulting in a total of seven peaks with the main peak around 25450 Da. Data do not indicate deglycosylation or polypeptide changes with storage time.

FIG. 3 shows similar peaks for the reference and the 12 months samples indicate no changes in MBL polypeptide chain during storage.

Discussion

The 1 mg/ml formulation is stable 12 months under frozen storage with no changes in C4-activation, no aggregates detected and no changes in polypeptide chain. Among other analyses performed are AIEC for content, non-reduced western blots for size distribution, coomasie staining for degradation products detection and amino acid analysis to verify content. None of these analyses indicate any change after 12 months storage at frozen and chilled temperatures. Approximately 99% of the total MBL elutes similar to reference MBL after 12 months storage at chilled temperature. C.

For the 10 mg/ml formulation a decrease in C4-activation is detected for all analysed samples to around 80% after both 2½ and 5 months of storage at frozen and chilled temperature, indicating that once MBL has been concentrated to 10 mg/ml it is stable. The C4-activation value at time zero are measured to 94%. SEC analyses indicate an aggregated amount around 4% for both 2½ and 5 months of storage at frozen and chilled temperature. The amount of aggregate is constant with temperature and storage time indicating that aggregate might be present from study start in the concentrated formulations and caused by the concentration step rather than by storage. Any formulation higher than 1 mg/ml has been prepared by concentration using a filtration device exposing the protein to 3500× G. A process step extremely stressful to any protein and a treatment generally known to cause protein aggregation.

The 5 mg/ml formulation has C4-activation results between 91 and 94% compared to the reference for storage at frozen, chilled and even at +37 degree. A control formulation without calcium placed at +37 degree is measured to 19% activity after two months of storage. SEC detects aggregation with amounts corresponding to 1 to 3% of total MBL content for frozen and chilled samples and 62% for the control at +37 degree. Samples are not analysed by Maldi-MS.

Data from the three stability studies all indicate MBL as an exceptionally stable protein at frozen and chilled storage. The final conclusion is that a highly stable 1 mg/ml liquid MBL formulation has been developed for parenteral use without any stabilizing excipients. The addition of Calcium has a dramatically stabilizing effect on a concentrated formulation. A 5 mg/ml formulation stored for two months at +37 degree without any activity loss is exceptional for protein formulations.

Example 9

C4 Activation Assay

Coating FluoroNunc Plates with Mannan.

FluoroNunc micro titer plates are coated with 100 µl/well of a solution containing 10 µg/ml of Mannan (Sigma-Aldrich, powder # M7504) dissolved in 50 mM $NaCO_3$ buffer pH 9.6 over night at 20±4° C. in a humidified chamber. Plates are washed twice in TBS (Tris (10 mM), NaCl (150 mM) pH 7.4 ) before blocking the plates for 1 hour at 20±4° C. with 200 µl per well of TBS buffer supplemented with 1 mg/ml HSA (Statens Serum Institute, Copenhagen). Each well is washed three times with TBST buffer.

C4 Activation Assay

MASP is purified from an MBL deficient individual without anti Mannan antibodies. The rMBL reference standard originate from a purified rMBL reference material that has been pre-diluted into LISA buffer (Tris/Base (20 mM), NaCl (150 mM), $CaCl_2$ (10 mM), HSA 1 mg/ml, Triton X-100 (0.05%), PH 7.4) to a final concentration of 100 µg/ml and stored at −80 degrees Celsius.

The rMBL standard and the test samples is pre-diluted to 5 µg/ml in LISA buffer. The pre-diluted rMBL standard and the samples are mixed with the MASP in a 1:1 volume and incubated for 10 min at 37 degrees Celsius.

C4 complement factor is purified from fresh blood and stored frozen in C4, 1 M NaCl, 20 mM Tris, 50 mM 6-amino-hexansyre, 5 mM EDTA, 0.02% W7v $NaN_3$ pH 7.4. C4 is thawed on ice and diluted 1:2000 in B1 buffer (Barbital (16 mM), NaCl (580 mM), $CaCl_2$(8 mM), $MgCl_2$ (4 mM) pH 7.4. Cat. No.210050 Bie Berntsen). Pre-diluted rMBL:MASP complex and the test samples are diluted 1:10 in the C4:B1 buffer and a dilution series of 2-fold dilutions are prepared.

The mannan coated plate is placed on ice and the samples are applied onto the plate. The reaction is initiated when the samples are transferred to the 37 degrees Celsius incubator.

The plate is incubated for 90 min at 37 degrees Celsius in a controlled incubator and washed three times in TBST/$Ca^{2+}$ buffer (Tris (10 mM), NaCl (150 mM), Tween-20 (0.05%w/v), $CaCl_2$ (100 mM) pH 7.4) in a plate washer. 100 µl per well of biotin-labelled human anti C4 antibody (Goat anti-human C4, from DAKO)(1 µg/ml) diluted 1:1000 in TBST/$Ca^{2+}$ buffer is added and incubated for 90 min at 25 degrees Celsius in a heating tower. Plates are washed three times in TBST/$Ca^{2+}$ buffer in a plate washer. 100 µl per well of Europium-streptavidin solution (Wallac 1244-360) is diluted 1:1000 in Europium dilution buffer (Tris (10 mM), NaCl (150 mM), Tween-20 (0.05%), EDTA (25 µM)) and incubated for 60 min at 25 degrees Celsius in a heating tower. Plates are washed three times in TBST/$Ca^{2+}$ buffer in the plate washer. 100 µl Enhancement solution (Wallac 1244-105) is added per well and the samples shaked for 5 min in a plate shaker. Samples are settled for approximately 5 min and inserted into a Wallac Victor $2^d$ Multicounter 1420. The fluorescence of $Eu^{3+}$ is measured using the standard Europium program.

The data obtained from the reading of the assay should be plotted as follows:

The MBL concentration at the x-axes and the Europium counts (the cpm) at the y-axes. The MBL concentration should be pictured as the natural log whereas the Europium should be the linear data.

For the data analysis and EC50 calculations use the Hill coefficient equation and 4 parameters.

The relative potency of the rMBL sample is determined from the rMBL reference standard as follows:

Relative potency=(EC50reference standard/EC50test)*100

Example 10

Size Exclusion Chromatography (SEC)

All samples for analysis should be free of visible precipitates and prepared in HPLC vials using caps with septa. The protein solution is applied to the Superose column at room temperature in a Tris-based buffer (pH=7.4).

The Superose 6 HR10/30 column is delivered pre-packed from Amersham Bio-sciences.

Chromatography is performed according to the below specification:

| | |
|---|---|
| Resin Type | Superose 6 |
| Resin Size | Area 0.78 cm$^2$, Height 30 cm |
| Temperature | 25° C. |
| Solvent Flow | 38 cm/hr (0.5 mL/min) during the complete chromatography |
| Gradient Profile | Isocratic; 40 mL elution buffer per run, corresponding to a runtime of 80 mins. |
| Detection | 280 nm (detection af protein) |
| | Sensitivity: AuxiliaryRange = 2, Range = 1, Response = 4 (important!) |
| Run Time | 80 min |
| Sampling Frequency | 5 Hz (each 0.2 s) |
| Solvents | |

| | | |
|---|---|---|
| Elution buffer (STOCK) | Tris (0.1 M) NaCl (1.4 M) NaN$_3$ (0.01% w/v) pH = 7.4 (20° C.) | Tris (24.2 g), NaCl (163.6 g) and 2.0 mL natriumazid (10%), are dissolved in H$_2$O (ad 2000 mL). During the process, pH is adjusted with 5 M HCl. Estimated storage time: Long |
| Elution buffer | Tris (10 mM) NaCl (140 mM) NaN$_3$ (0.001% w/v) pH = 7.4 (20° C.) | Elutionbuffer(STOCK) (200 mL) is diluted into water (ad 2000 mL). pH in the final solution should be controlled. Estimated storage time: Medium |
| Regeneration buffer (Acid) | HCl (0.1 M) | HCl (5 M, 10 mL) is dissolved in H$_2$O (ad 500 mL). Estimated storage time: Long |
| Regeneration buffer (Alkaline) | NaOH (0.5 M) | NaOH (20 g) is dissolved in H20 (ad 1000 mL). Estimated storage time: Long |

REFERENCES

Akers, J. M. and Defelippis, R. M., 2000, Pharmaceutical Formulation Development of Peptides and Proteins, edited by S. Frokjaer and L. Hovgaard, pp.166-167, London: Taylor and Francis.

Davies, E. J., Snowden, N., Hillarby, M. C., Carthy, D. Grennan, D. M., Thomson, W. and Ollier, W. E. R. Mannose-binding protein gene polymorphism in systemic lupus erythematosus. Arthritis Rheum. 38, 110-114 (1995).

Frokjaer, S. and Hovgaard, L., Pharmaceutical formulation development of peptides and proteins, Taylor and Francis, pp. 100-109.

Garred, P., Madsen, H. O., Hofmann, B. & Svejgaard, A. Increased frequency of homozygosity of abnormal mannan-binding-protein alleles in patients with suspected immunodeficiency. *Lancet* 346, 941-943 (1995).

Garred, P., Madsen, H. O., Balslev, U., Hofmann, B., Pedersen, C., Gerstoft, J. and Svejgaard, A. Susceptibility to HIV infection and progression of AIDS in relation to variant alleles of mannose-binding lectin. Lancet 349, 236-240 (1997).

Ji, Y -H. et al. Activation of the C4 and C2 components of complement by a proteinase in serum bactericidal factor, Ra reactive factor *J. Immunol.* 150, 571-578 (1993).

Kawasaki, N., Kawasaki, T. & Yamashina, I. A serum lectin (mannan-binding protein) has complement-dependent bactericidal activity. *J. Biochem.* 106, 483-489 (1989).

Kilpatrick, D. C., Bevan, B. H. and Liston, W. A. Association between mannan-binding protein deficiency and recurrent miscarriage. Mol. Hum. Reprod. 1, 2501-2505 (1995).

Kuhlman, M., Joiner, K. & Ezekowitz, R. A. B. The human mannose-binding protein functions as an opsonin. *J. Exp. Med.* 169, 1733-1745 (1989).

Lipscombe, R. J. et al. High frequencies in African and non-African populations of independent mutations in the mannose binding protein gene. *Hum. Mol. Genet.* 1, 709-715 (1992).

Lipscombe R J, et al: Distinct physicochemical characteristics of human mannose binding protein expressed by individuals of differing genotype, Immunology 85 (1995) 660-667

Madsen H. O. et al. A new frequent allele is the missing link in the structural poly-morphism of the human mannan-binding protein. *Immunogenetics* 40, 3744 (1994).

Malhotra, R. Wormald, M. R., Rudd, P. M., Fischer, P. B., Dwek, R. A. and Sim, R. B. Glycosylation changes of IgG associated with rheumatoid arthritis can activate complement via the mannose-binding protein. Nature Med. 1, 237- 243 (1995).

Matsushita, M. & Fujita, T. 4) Activation of the classical complement pathway by mannose-binding protein in association with a novel C1s-like serine protease *J. Exp. Med.* 176, 1497-1502 (1992).

Nema S, Washkuhn R J and Brendel R J, 1997, Journal of Pharmaceutical Science & Technology, 51:166-171

Nielsen, S. L., Andersen, P. L., Koch, C., Jensenius, J. C. & Thiel, S. The level of the serum opsonin, mannan-binding protein in HIV-1 antibody-positive patients. *Clin. Exp. Immunol.* 100, 219-222 (1995).

Sumiya, M. et al. Molecular basis of opsonic defect in immunodeficient children. *Lancet* 337, 1569-1570 (1991).

Super, M., Thiel, S., Lu, J., Levinsky, R. J. & Turner, M. W. Association of low levels of mannan-binding protein with a common defect of opsonisation. *Lancet* ii, 1236-1239 (1989).

Summerfield, J. A. et al. Mannose binding protein gene mutations associated with unusual and severe infections in adults. *Lancet* 345, 886-889 (1995).

Thiel, S., Vorup-Jensen, T., Stover, C. M., Schwable, W., Laursen, S. B., Poulsen, K., Willis, A. C., Eggleton, P., Hansen, S., Holmskov, U., Reid, K. B. M., Jensenius, J. C. (1997), A second serine protease associated with mannan-binding lectin that activates complement, Nature, 386, 506-510.

Turner, M. W. Mannose-binding lectin: the pluripotent molecule of the innate immune system. *Immunol. Today,* 17, 532-540 (1996).

Valdimarson et al., 1998, Scand. J. Immunol. 48:116-123

Vorup-Jensen T et al: Recombinant expression of human mannan-binding lectin, Int Immunopharm 1 (2001) 677-687

---

The invention claimed is:

1. A stable, sterile filtered, pharmaceutically acceptable composition comprising
   at least 750 µg/ml mannan binding lectin (MBL) and/or at least one MBL functional homologue which is at least 95% identical with SEQ ID NO:1, or a salt thereof, and an MBL-stabilizing amount of a divalent cation,
   wherein said composition is free of any protein containing stabiliser, and wherein each said MBL functional homologue has C4 activation activity.

2. The composition according to claim 1, wherein the composition is a protein solution.

3. The composition according to claim 1, wherein the composition is a protein suspension.

4. The composition according to any of claim 2, wherein the solution or suspension is frozen.

5. The composition according to claim 1, wherein the composition is a dry composition, comprising freeze-dried protein.

6. The composition according to claim 5, wherein said dry composition is capable of being reconstituted into a solution.

7. The composition according to claim 1, wherein said solution or suspension is suitable for administration by injection or infusion.

8. The composition according to claim 1, wherein said solution or suspension is suitable for administration as bolus injection.

9. The composition according to claim 1, wherein said solution or suspension is suitable for administration by intravenous injection or infusion.

10. The composition according to claim 1, wherein said solution or suspension is suitable for administration by subcutaneous injection.

11. The composition according to claim 1, wherein said solution or suspension is suitable for administration by intramuscular injection.

12. The composition according to claim 1, wherein the composition comprises at least 750 µg/ml MBL or MBL salts.

13. The composition according to claim 1, wherein the total protein furthermore comprises one or more MBL associated serine protease (MASP) or fragments thereof.

14. The composition according to claim 1, wherein the total protein further comprises at least one polypeptide which is (a) MEL associated serine protease (MASP),
   wherein said MASP is selected from the group consisting of MASP-1 of SEQ ID NO:2, MASP2 of SEQ ID NO:3, and MASP-3 of SEQ ID NO:4, or (b) a functional homologue of (a), where said functional homologue is at least 95% identical with (a) above.

15. The composition according to claim 1, wherein MBL is purified naturally occurring human serum MBL.

16. The composition according to claim 1, wherein at least one of said MBL or said MBL functional homologues has been recombinantly produced.

17. The composition according to claim 16, wherein more than 50% of MBL is bigger than 200 kDa as determined by non-reducing SDS-PAGE.

18. The composition according to claim 1, further comprising an isotonic agent.

19. The composition according to claim 1, further comprising a buffer.

20. The composition according to claim 1, further comprising a non-(protein-containing) stabiliser.

21. The compositions according to claim 1, wherein the divalent cation is selected from the group consisting of $Ca^{++}$, $Ni^{++}$, $Mg^{++}$, and $Mn^{++}$.

22. The composition according to claim 1, wherein the divalent cation is $Ca^{++}$.

23. The composition according to claim 5, further comprising one or more pharmaceutically acceptable additives selected from the group consisting of isotonic agents, buffer, non-(protein-containing) stabilisers and cryoprotectant agents.

24. The composition according to claim 5, further comprising one or more pharmaceutically acceptable additives selected from the group consisiting of glucosemonohydrate, glycine, NaCl and polyethyleneglycol 3350.

25. The composition according to claim 19, wherein the buffer is capable of buffering a solution to a pH in the range of 6 to 8.

26. The composition according to claim 19, wherein the buffer is selected from the group consisting of TRIS, phosphate, citrate, carbonate, glycinate, histidine, glycine, succinate and triethanolamine buffer.

27. The composition according to claim 18, wherein the isotonic agent is selected from the group consisting of NaCl, $CaCl_2$, KCl, $MgCl_2$, mannitol and glycerol.

28. The composition according to claim 20, wherein the stabiliser is selected from the group consisting of poloxamers, Tween-20, Tween-40, Tween-60, Tween-80, metal ions, amino acids, polyethylene glucol, Triton, EDTA and ascorbic acid.

29. The composition according to claim 23, wherein said cryoprotectant agent is selected from the group consisting of dextran, polyethylenglycol, sucrose, trehalose and mannitol.

30. The composition according to claim 1, wherein the composition does not comprise detergents.

31. A method of treatment of a clinical condition in an individual in need thereof, said clinical condition selected from the group consisitng of infections, MBL deficiency and immunocompromised conditions, comprising administration of a pharmaceutical composition according to claim 1.

32. The method according to claim 31, wherein the treatment is an ameliorating treatment.

33. The method according to claim 31, wherein administration is by injection or infusion.

34. The method according to claim 31, wherein administration is as bolus injection.

35. The method according to claim 31, wherein administration is by intravenous injection or infusion.

36. The method according to claim 31, wherein administration is by subcutaneous injection.

37. The method according to claim 31, wherein administration is by intramuscular injection.

38. The method according to claim 31, wherein the clinical condition is an infection.

39. The method according to claim 31, wherein the individual is a human being.

40. The method according to claim 31, wherein the individual is a human being suffering from an increased risk of acquiring an infection.

41. The method according to claim 31, wherein the individual is a human being with subnormal serum MBL level.

42. The composition of claim 1, wherein said composition is also free of detergent.

43. The composition of claim 1, in which the MBL functional homologues, if any, are fragments of SEQ ID NO:1.

44. The composition of claim 12, wherein, after storage for two months at 37° C., the composition retains at least 80% of the original C4 activation activity.

45. The composition of claim 12, which retains at least 50% of the original C4 activation activity after five months storage at −20° C.

46. The composition of claim 12, which retains at least 50% of the original C4 activation activity after five months storage at 4° C.

47. The composition of claim 12, which retains at least 50% of the original C4 activation activity after 12 months storage at −20 °0 C.

48. The composition of claim 12, which retains at least 50% of the original C4 activation activity after 6 months storage at 37° C.

49. The composition of claim 1, which
(1) retains at least 50% of the original C4 activation activity after five months storage at 4° C, and/or
(2) retains at least 50% of the original C4 activation activity after 12 months storage at −20° C.

50. The composition of claim 1, wherein the composition does not comprise stabilizers, other than divalent cations.

51. The composition of claim 1, wherein the sequence which is at least 95% identical with SEQ ID NO:1 differs from SEQ ID NO:1 solely by one or more substitutions.

52. The composition of claim 1, wherein the sequence which is at least 95% identical with SEQ ID NO:1 differs from SEQ ID NO:1 solely by one or more conservative substitutions.

53. The composition of claim 1, wherein said functional homologue comprises a sequence which is at least 96% identical with SEQ ID NO:1.

54. The composition of claim 1, wherein said functional homologue comprises a sequence which is at least 97% identical with SEQ ID NO:1.

55. The composition of claim 1, wherein said functional homologue comprises a sequence which is at least 98% identical with SEQ ID NO:1.

56. The composition of claim 1, wherein said functional homologue comprises a sequence which is at least 99% identical with SEQ ID NO:1.

57. The composition of claim 51, where said difference is not more than eight substitutions.

58. The composition of claim 51, where said difference is not more than six substitutions.

59. The composition of claim 51, where said difference is not more than four substitutions.

60. The composition of claim 51, where said difference is not more than two substitutions.

61. The composition of claim 51, where said difference is not more than one substitution.

62. The composition of claim 52, where there are not more than two conservative substitutions.

63. The composition of claim 52, where there is not more than one conservative substitution.

64. The composition of claim 12, which comprises at least 1000 μg/mL of MBL.

65. The composition of claim 12, which comprises at least 1,500 μg/mL of MBL.

66. The composition of claim 12, which comprises at least 2,000 μg/mL of MBL.

67. The composition of claim 12, which comprises at least 2,500 μg/mL of MBL.

68. The composition of claim 12, which comprises at least 3,000 μg/mL of MBL.

69. The composition of claim 12, which comprises at least 3,500 μg/mL of MBL.

70. The composition of claim 12, which comprises at least 4,000 μg/mL of MBL.

71. The composition of claim 12, which comprises at least 5,000 μg/mL of MBL.

72. The composition of claim 12, which comprises at least 10,000 μg/mL of MBL.

73. The composition of claim 1, characterized by a concentration of 1,000-10,000 μg/mL of MBL and/or at least one MBL functional homologue.

74. The composition according to claim 12, wherein MBL constitutes at least 70% (w/w) of the total protein.

75. The composition of claim 12, wherein the composition does not comprise stabilizers, other than divalent cations.

76. The composition according to claim 12, wherein MBL constitutes at least 80% (w/w) of the total protein.

77. The composition according to claim 12, wherein MBL constitutes at least 90% (w/w) of the total protein.

78. The composition according to claim 12, wherein the divalent cation is $Ca^{++}$.

79. The composition according to claim 12, wherein the divalent cation is provided in a concentration of 0.01 mM to 1000 mM.

80. The composition according to claim 1, wherein the divalent cation is provided in a concentration of 0.05 mM to 500 mM.

81. The composition according to claim 1, wherein the divalent cation is provided in a concentration of 0.1 mM to 100 mM.

82. The composition according to claim 1, wherein the divalent cation is provided in a concentration of 0.2 mM to 50 mM.

83. The composition according to claim 1, wherein the divalent cation is provided in a concentration of 0.5 mM to 10 mM.

84. The composition according to claim 1, wherein the divalent cation is provided in a concentration of 0.5 mM to 2 mM.

85. The composition according to claim 12, wherein the divalent cation is provided in a concentration of 0.01 mM to 1000 mM.

86. The composition according to claim 12, wherein the divalent cation is provided in a concentration of 0.1 mM to 100 mM.

87. The composition according to claim 12, wherein the divalent cation is provided in a concentration of 0.5 mM to 10 mM.

88. The composition according to claim 22, wherein the divalent cation is provided in a concentration of 0.01 mM to 1000 mM.

89. The composition according to claim 22, wherein the divalent cation is provided in a concentration of 0.1 mM to 100 mM.

90. The composition according to claim 22, wherein the divalent cation is provided in a concentration of 0.5 mM to 10 mM.

91. The composition according to claim 78, wherein the divalent cation is provided in a concentration of 0.01 mM to 1000 mM.

92. The composition according to claim 78, wherein the divalent cation is provided in a concentration of 0.1 mM to 100 mM.

93. The composition according to claim 78, wherein the divalent cation is provided in a concentration of 0.5 mM to 10 mM.

94. The composition according to claim 78, wherein the divalent cation is provided in a concentration of 0.5 mM to 2 mM.

95. The composition according to claim 64, wherein the divalent cation is $Ca^{++}$.

96. The composition according to claim 66, wherein the divalent cation is $Ca^{++}$.

97. The composition according to claim 71, wherein the divalent cation is $Ca^{++}$.

98. The composition according to claim 95, wherein the divalent cation is provided in a concentration of 0.01 mM to 1000 mM.

99. The composition according to claim 95, wherein the divalent cation is provided in a concentration of 0.1 mM to 100 mM.

100. The composition according to claim 95, wherein the divalent cation is provided in a concentration of 0.5 mM to 10 mM.

101. The composition according to claim 96, wherein the divalent cation is provided in a concentration of 0.01 mM to 1000 mM.

102. The composition according to claim 96, wherein the divalent cation is provided in a concentration of 0.1 mM to 100 mM.

103. The composition according to claim 96, wherein the divalent cation is provided in a concentration of 0.5 mM to 10 mM.

104. The composition of claim 12, wherein the MBL concentration is greater than 1 mg/ml.

105. The composition of claim 104, wherein the MPL was concentrated at least in part by centrifugation.

106. The composition of claim 104, wherein aggregated MBL, other than normal oligomeric MBL, is not more than about 5% of total MBL.

* * * * *

SEQUENCE LISTING

```
<160> NUMBER OF SEQ ID NOS: 4

<210> SEQ ID NO 1
<211> LENGTH: 248
<212> TYPE: PRT
<213> ORGANISM: Homo Sapiens

<400> SEQUENCE: 1

Met Ser Leu Phe Pro Ser Leu Pro Leu Leu Leu Leu Ser Met Val Ala
1               5                   10                  15

Ala Ser Tyr Ser Glu Thr Val Thr Cys Glu Asp Ala Gln Lys Thr Cys
            20                  25                  30

Pro Ala Val Ile Ala Cys Ser Ser Pro Gly Ile Asn Gly Phe Pro Gly
        35                  40                  45

Lys Asp Gly Arg Asp Gly Thr Lys Gly Glu Lys Gly Glu Pro Gly Gln
    50                  55                  60

Gly Leu Arg Gly Leu Gln Gly Pro Pro Gly Lys Leu Gly Pro Pro Gly
65                  70                  75                  80

Asn Pro Gly Pro Ser Gly Ser Pro Gly Pro Lys Gly Gln Lys Gly Asp
                85                  90                  95

Pro Gly Lys Ser Pro Asp Gly Asp Ser Ser Leu Ala Ala Ser Glu Arg
            100                 105                 110

Lys Ala Leu Gln Thr Glu Met Ala Arg Ile Lys Lys Trp Leu Thr Phe
        115                 120                 125

Ser Leu Gly Lys Gln Val Gly Asn Lys Phe Phe Leu Thr Asn Gly Glu
    130                 135                 140

Ile Met Thr Phe Glu Lys Val Lys Ala Leu Cys Val Lys Phe Gln Ala
145                 150                 155                 160

Ser Val Ala Thr Pro Arg Asn Ala Ala Glu Asn Gly Ala Ile Gln Asn
                165                 170                 175

Leu Ile Lys Glu Glu Ala Phe Leu Gly Ile Thr Asp Glu Lys Thr Glu
            180                 185                 190

Gly Gln Phe Val Asp Leu Thr Gly Asn Arg Leu Thr Tyr Thr Asn Trp
        195                 200                 205

Asn Glu Gly Glu Pro Asn Asn Ala Gly Ser Asp Glu Asp Cys Val Leu
    210                 215                 220

Leu Leu Lys Asn Gly Gln Trp Asn Asp Val Pro Cys Ser Thr Ser His
225                 230                 235                 240

Leu Ala Val Cys Glu Phe Pro Ile
                245
```

<210> SEQ ID NO 2
<211> LENGTH: 699
<212> TYPE: PRT
<213> ORGANISM: Homo Sapiens

<400> SEQUENCE: 2

```
Met Arg Trp Leu Leu Tyr Tyr Ala Leu Cys Phe Ser Leu Ser Lys
1               5                   10                  15

Ala Ser Ala His Thr Val Glu Leu Asn Asn Met Phe Gly Gln Ile Gln
            20                  25                  30

Ser Pro Gly Tyr Pro Asp Ser Tyr Pro Ser Asp Ser Glu Val Thr Trp
        35                  40                  45

Asn Ile Thr Val Pro Asp Gly Phe Arg Ile Lys Leu Tyr Phe Met His
    50                  55                  60

Phe Asn Leu Glu Ser Ser Tyr Leu Cys Glu Tyr Asp Tyr Val Lys Val
65                  70                  75                  80

Glu Thr Glu Asp Gln Val Leu Ala Thr Phe Cys Gly Arg Glu Thr Thr
                85                  90                  95

Asp Thr Glu Gln Thr Pro Gly Gln Glu Val Val Leu Ser Pro Gly Ser
            100                 105                 110

Phe Met Ser Ile Thr Phe Arg Ser Asp Phe Ser Asn Glu Glu Arg Phe
        115                 120                 125

Thr Gly Phe Asp Ala His Tyr Met Ala Val Asp Val Asp Glu Cys Lys
    130                 135                 140

Glu Arg Glu Asp Glu Glu Leu Ser Cys Asp His Tyr Cys His Asn Tyr
145                 150                 155                 160

Ile Gly Gly Tyr Tyr Cys Ser Cys Arg Phe Gly Tyr Ile Leu His Thr
                165                 170                 175

Asp Asn Arg Thr Cys Arg Val Glu Cys Ser Asp Asn Leu Phe Thr Gln
            180                 185                 190

Arg Thr Gly Val Ile Thr Ser Pro Asp Phe Pro Asn Pro Tyr Pro Lys
        195                 200                 205

Ser Ser Glu Cys Leu Tyr Thr Ile Glu Leu Glu Glu Gly Phe Met Val
    210                 215                 220

Asn Leu Gln Phe Glu Asp Ile Phe Asp Ile Glu Asp His Pro Glu Val
225                 230                 235                 240

Pro Cys Pro Tyr Asp Tyr Ile Lys Ile Lys Val Gly Pro Lys Val Leu
                245                 250                 255

Gly Pro Phe Cys Gly Glu Lys Ala Pro Glu Pro Ile Ser Thr Gln Ser
            260                 265                 270

His Ser Val Leu Ile Leu Phe His Ser Asp Asn Ser Gly Glu Asn Arg
        275                 280                 285

Gly Trp Arg Leu Ser Tyr Arg Ala Ala Gly Asn Glu Cys Pro Glu Leu
    290                 295                 300

Gln Pro Pro Val His Gly Lys Ile Glu Pro Ser Gln Ala Lys Tyr Phe
305                 310                 315                 320

Phe Lys Asp Gln Val Leu Val Ser Cys Asp Thr Gly Tyr Lys Val Leu
                325                 330                 335

Lys Asp Asn Val Glu Met Asp Thr Phe Gln Ile Glu Cys Leu Lys Asp
            340                 345                 350

Gly Thr Trp Ser Asn Lys Ile Pro Thr Cys Lys Ile Val Asp Cys Arg
        355                 360                 365

Ala Pro Gly Glu Leu Glu His Gly Leu Ile Thr Phe Ser Thr Arg Asn
```

```
                370             375             380
Asn Leu Thr Thr Tyr Lys Ser Glu Ile Lys Tyr Ser Cys Gln Glu Pro
385                 390                 395                 400

Tyr Tyr Lys Met Leu Asn Asn Asn Thr Gly Ile Tyr Thr Cys Ser Ala
                405                 410                 415

Gln Gly Val Trp Met Asn Lys Val Leu Gly Arg Ser Leu Pro Thr Cys
            420                 425                 430

Leu Pro Val Cys Gly Leu Pro Lys Phe Ser Arg Lys Leu Met Ala Arg
        435                 440                 445

Ile Phe Asn Gly Arg Pro Ala Gln Lys Gly Thr Thr Pro Trp Ile Ala
    450                 455                 460

Met Leu Ser His Leu Asn Gly Gln Pro Phe Cys Gly Gly Ser Leu Leu
465                 470                 475                 480

Gly Ser Ser Trp Ile Val Thr Ala Ala His Cys Leu His Gln Ser Leu
                485                 490                 495

Asp Pro Lys Asp Pro Thr Leu Arg Asp Ser Asp Leu Leu Ser Pro Ser
            500                 505                 510

Asp Phe Lys Ile Ile Leu Gly Lys His Trp Arg Leu Arg Ser Asp Glu
        515                 520                 525

Asn Glu Gln His Leu Gly Val Lys His Thr Thr Leu His Pro Lys Tyr
    530                 535                 540

Asp Pro Asn Thr Phe Glu Asn Asp Val Ala Leu Val Glu Leu Leu Glu
545                 550                 555                 560

Ser Pro Val Leu Asn Ala Phe Val Met Pro Ile Cys Leu Pro Glu Gly
                565                 570                 575

Pro Gln Gln Glu Gly Ala Met Val Ile Val Ser Gly Trp Gly Lys Gln
            580                 585                 590

Phe Leu Gln Arg Phe Pro Glu Thr Leu Met Glu Ile Glu Ile Pro Ile
        595                 600                 605

Val Asp His Ser Thr Cys Gln Lys Ala Tyr Ala Pro Leu Lys Lys Lys
    610                 615                 620

Val Thr Arg Asp Met Ile Cys Ala Gly Glu Lys Glu Gly Gly Lys Asp
625                 630                 635                 640

Ala Cys Ser Gly Asp Ser Gly Gly Pro Met Val Thr Leu Asn Arg Glu
                645                 650                 655

Arg Gly Gln Trp Tyr Leu Val Gly Thr Val Ser Trp Gly Asp Asp Cys
            660                 665                 670

Gly Lys Lys Asp Arg Tyr Gly Val Tyr Ser Tyr Ile His His Asn Lys
        675                 680                 685

Asp Trp Ile Gln Arg Val Thr Gly Val Arg Asn
    690                 695

<210> SEQ ID NO 3
<211> LENGTH: 686
<212> TYPE: PRT
<213> ORGANISM: Homo Sapiens

<400> SEQUENCE: 3

Met Arg Leu Leu Thr Leu Leu Gly Leu Leu Cys Gly Ser Val Ala Thr
1               5                   10                  15

Pro Leu Gly Pro Lys Trp Pro Glu Pro Val Phe Gly Arg Leu Ala Ser
                20                  25                  30

Pro Gly Phe Pro Gly Glu Tyr Ala Asn Asp Gln Glu Arg Arg Trp Thr
            35                  40                  45
```

```
Leu Thr Ala Pro Pro Gly Tyr Arg Leu Arg Leu Tyr Phe Thr His Phe
 50                  55                  60

Asp Leu Glu Leu Ser His Leu Cys Glu Tyr Asp Phe Val Lys Leu Ser
 65                  70                  75                  80

Ser Gly Ala Lys Val Leu Ala Thr Leu Cys Gly Gln Glu Ser Thr Asp
                 85                  90                  95

Thr Glu Arg Ala Pro Gly Lys Asp Thr Phe Tyr Ser Leu Gly Ser Ser
            100                 105                 110

Leu Asp Ile Thr Phe Arg Ser Asp Tyr Ser Asn Glu Lys Pro Phe Thr
            115                 120                 125

Gly Phe Glu Ala Phe Tyr Ala Ala Glu Asp Ile Asp Glu Cys Gln Val
130                 135                 140

Ala Pro Gly Glu Ala Pro Thr Cys Asp His His Cys His Asn His Leu
145                 150                 155                 160

Gly Gly Phe Tyr Cys Ser Cys Arg Ala Gly Tyr Val Leu His Arg Asn
                165                 170                 175

Lys Arg Thr Cys Ser Ala Leu Cys Ser Gly Gln Val Phe Thr Gln Arg
            180                 185                 190

Ser Gly Glu Leu Ser Ser Pro Glu Tyr Pro Arg Pro Tyr Pro Lys Leu
            195                 200                 205

Ser Ser Cys Thr Tyr Ser Ile Ser Leu Glu Glu Gly Phe Ser Val Ile
210                 215                 220

Leu Asp Phe Val Glu Ser Phe Asp Val Glu Thr His Pro Glu Thr Leu
225                 230                 235                 240

Cys Pro Tyr Asp Phe Leu Lys Ile Gln Thr Asp Arg Glu Glu His Gly
                245                 250                 255

Pro Phe Cys Gly Lys Thr Leu Pro His Arg Ile Glu Thr Lys Ser Asn
            260                 265                 270

Thr Val Thr Ile Thr Phe Val Thr Asp Glu Ser Gly Asp His Thr Gly
            275                 280                 285

Trp Lys Ile His Tyr Thr Ser Thr Ala His Ala Cys Pro Tyr Pro Met
290                 295                 300

Ala Pro Pro Asn Gly His Val Ser Pro Val Gln Ala Lys Tyr Ile Leu
305                 310                 315                 320

Lys Asp Ser Phe Ser Ile Phe Cys Glu Thr Gly Tyr Glu Leu Leu Gln
                325                 330                 335

Gly His Leu Pro Leu Lys Ser Phe Thr Ala Val Cys Gln Lys Asp Gly
            340                 345                 350

Ser Trp Asp Arg Pro Met Pro Ala Cys Ser Ile Val Asp Cys Gly Pro
            355                 360                 365

Pro Asp Asp Leu Pro Ser Gly Arg Val Glu Tyr Ile Thr Gly Pro Gly
370                 375                 380

Val Thr Thr Tyr Lys Ala Val Ile Gln Tyr Ser Cys Glu Glu Thr Phe
385                 390                 395                 400

Tyr Thr Met Lys Val Asn Asp Gly Lys Tyr Val Cys Glu Ala Asp Gly
                405                 410                 415

Phe Trp Thr Ser Ser Lys Gly Glu Lys Ser Leu Pro Val Cys Glu Pro
            420                 425                 430

Val Cys Gly Leu Ser Ala Arg Thr Thr Gly Gly Arg Ile Tyr Gly Gly
            435                 440                 445

Gln Lys Ala Lys Pro Gly Asp Phe Pro Trp Gln Val Leu Ile Leu Gly
450                 455                 460

Gly Thr Thr Ala Ala Gly Ala Leu Leu Tyr Asp Asn Trp Val Leu Thr
```

```
                        465                 470                 475                 480
Ala Ala His Ala Val Tyr Glu Gln Lys His Asp Ala Ser Ala Leu Asp
                    485                 490                 495

Ile Arg Met Gly Thr Leu Lys Arg Leu Ser Pro His Tyr Thr Gln Ala
                500                 505                 510

Trp Ser Glu Ala Val Phe Ile His Glu Gly Tyr Thr His Asp Ala Gly
                515                 520                 525

Phe Asp Asn Asp Ile Ala Leu Ile Lys Leu Asn Asn Lys Val Val Ile
            530                 535                 540

Asn Ser Asn Ile Thr Pro Ile Cys Leu Pro Arg Lys Glu Ala Glu Ser
545                 550                 555                 560

Phe Met Arg Thr Asp Asp Ile Gly Thr Ala Ser Gly Trp Gly Leu Thr
                565                 570                 575

Gln Arg Gly Phe Leu Ala Arg Asn Leu Met Tyr Val Asp Ile Pro Ile
            580                 585                 590

Val Asp His Gln Lys Cys Thr Ala Ala Tyr Glu Lys Pro Pro Tyr Pro
            595                 600                 605

Arg Gly Ser Val Thr Ala Asn Met Leu Cys Ala Gly Leu Glu Ser Gly
        610                 615                 620

Gly Lys Asp Ser Cys Arg Gly Asp Ser Gly Gly Ala Leu Val Phe Leu
625                 630                 635                 640

Asp Ser Glu Thr Glu Arg Trp Phe Val Gly Gly Ile Val Ser Trp Gly
                645                 650                 655

Ser Met Asn Cys Gly Glu Ala Gly Gln Tyr Gly Val Tyr Thr Lys Val
                660                 665                 670

Ile Asn Tyr Ile Pro Trp Ile Glu Asn Ile Ile Ser Asp Phe
            675                 680                 685

<210> SEQ ID NO 4
<211> LENGTH: 728
<212> TYPE: PRT
<213> ORGANISM: Homo Sapiens

<400> SEQUENCE: 4

Met Arg Trp Leu Leu Leu Tyr Tyr Ala Leu Cys Phe Ser Leu Ser Lys
1               5                   10                  15

Ala Ser Ala His Thr Val Glu Leu Asn Asn Met Phe Gly Gln Ile Gln
                20                  25                  30

Ser Pro Gly Tyr Pro Asp Ser Tyr Pro Ser Asp Ser Glu Val Thr Trp
            35                  40                  45

Asn Ile Thr Val Pro Asp Gly Phe Arg Ile Lys Leu Tyr Phe Met His
        50                  55                  60

Phe Asn Leu Glu Ser Ser Tyr Leu Cys Glu Tyr Asp Tyr Val Lys Val
65                  70                  75                  80

Glu Thr Glu Asp Gln Val Leu Ala Thr Phe Cys Gly Arg Glu Thr Thr
                85                  90                  95

Asp Thr Glu Gln Thr Pro Gly Gln Glu Val Val Leu Ser Pro Gly Ser
            100                 105                 110

Phe Met Ser Ile Thr Phe Arg Ser Asp Phe Ser Asn Glu Glu Arg Phe
        115                 120                 125

Thr Gly Phe Asp Ala His Tyr Met Ala Val Asp Val Asp Glu Cys Lys
    130                 135                 140

Glu Arg Glu Asp Glu Glu Leu Ser Cys Asp His Tyr Cys His Asn Tyr
145                 150                 155                 160
```

-continued

```
Ile Gly Gly Tyr Tyr Cys Ser Cys Arg Phe Gly Tyr Ile Leu His Thr
            165                 170                 175

Asp Asn Arg Thr Cys Arg Val Glu Cys Ser Asp Asn Leu Phe Thr Gln
            180                 185                 190

Arg Thr Gly Val Ile Thr Ser Pro Asp Phe Pro Asn Pro Tyr Pro Lys
            195                 200                 205

Ser Ser Glu Cys Leu Tyr Thr Ile Glu Leu Glu Glu Gly Phe Met Val
210                 215                 220

Asn Leu Gln Phe Glu Asp Ile Phe Asp Ile Glu Asp His Pro Glu Val
225                 230                 235                 240

Pro Cys Pro Tyr Asp Tyr Ile Lys Ile Lys Val Gly Pro Lys Val Leu
                245                 250                 255

Gly Pro Phe Cys Gly Glu Lys Ala Pro Glu Pro Ile Ser Thr Gln Ser
            260                 265                 270

His Ser Val Leu Ile Leu Phe His Ser Asp Asn Ser Gly Glu Asn Arg
            275                 280                 285

Gly Trp Arg Leu Ser Tyr Arg Ala Ala Gly Asn Glu Cys Pro Glu Leu
            290                 295                 300

Gln Pro Pro Val His Gly Lys Ile Glu Pro Ser Gln Ala Lys Tyr Phe
305                 310                 315                 320

Phe Lys Asp Gln Val Leu Val Ser Cys Asp Thr Gly Tyr Lys Val Leu
                325                 330                 335

Lys Asp Asn Val Glu Met Asp Thr Phe Gln Ile Glu Cys Leu Lys Asp
            340                 345                 350

Gly Thr Trp Ser Asn Lys Ile Pro Thr Cys Lys Ile Val Asp Cys Arg
            355                 360                 365

Ala Pro Gly Glu Leu Glu His Gly Leu Ile Thr Phe Ser Thr Arg Asn
370                 375                 380

Asn Leu Thr Thr Tyr Lys Ser Glu Ile Lys Tyr Ser Cys Gln Glu Pro
385                 390                 395                 400

Tyr Tyr Lys Met Leu Asn Asn Asn Thr Gly Ile Tyr Thr Cys Ser Ala
                405                 410                 415

Gln Gly Val Trp Met Asn Lys Val Leu Gly Arg Ser Leu Pro Thr Cys
            420                 425                 430

Leu Pro Glu Cys Gly Gln Pro Ser Arg Ser Leu Pro Ser Leu Val Lys
            435                 440                 445

Arg Ile Ile Gly Gly Arg Asn Ala Glu Pro Gly Leu Phe Pro Trp Gln
450                 455                 460

Ala Leu Ile Val Val Glu Asp Thr Ser Arg Val Pro Asn Asp Lys Trp
465                 470                 475                 480

Phe Gly Ser Gly Ala Leu Leu Ser Ala Ser Trp Ile Leu Thr Ala Ala
                485                 490                 495

His Val Leu Arg Ser Gln Arg Arg Asp Thr Thr Val Ile Pro Val Ser
            500                 505                 510

Lys Glu His Val Thr Val Tyr Leu Gly Leu His Asp Val Arg Asp Lys
            515                 520                 525

Ser Gly Ala Val Asn Ser Ser Ala Ala Arg Val Val Leu His Pro Asp
            530                 535                 540

Phe Asn Ile Gln Asn Tyr Asn His Asp Ile Ala Leu Val Gln Leu Gln
545                 550                 555                 560

Glu Pro Val Pro Leu Gly Pro His Val Met Pro Val Cys Leu Pro Arg
                565                 570                 575

Leu Glu Pro Glu Gly Pro Ala Pro His Met Leu Gly Leu Val Ala Gly
```

```
                                       -continued
              580                    585                     590

Trp Gly Ile Ser Asn Pro Asn Val Thr Val Asp Glu Ile Ile Ser Ser
            595                 600                 605

Gly Thr Arg Thr Leu Ser Asp Val Leu Gln Tyr Val Lys Leu Pro Val
            610                 615                 620

Val Pro His Ala Glu Cys Lys Thr Ser Tyr Glu Ser Arg Ser Gly Asn
625                 630                 635                 640

Tyr Ser Val Thr Glu Asn Met Phe Cys Ala Gly Tyr Tyr Glu Gly Gly
                645                 650                 655

Lys Asp Thr Cys Leu Gly Asp Ser Gly Gly Ala Phe Val Ile Phe Asp
                660                 665                 670

Asp Leu Ser Gln Arg Trp Val Val Gln Gly Leu Val Ser Trp Gly Gly
            675                 680                 685

Pro Glu Glu Cys Gly Ser Lys Gln Val Tyr Gly Val Tyr Thr Lys Val
            690                 695                 700

Ser Asn Tyr Val Asp Trp Val Trp Glu Gln Met Gly Leu Pro Gln Ser
705                 710                 715                 720

Val Val Glu Pro Gln Val Glu Arg
                725
```